United States Patent
Bostrom et al.

(10) Patent No.: US 10,629,403 B1
(45) Date of Patent: Apr. 21, 2020

(54) MAGNETIC ASSIST BEARING

(71) Applicant: Varex Imaging Corporation, Salt Lake City, UT (US)

(72) Inventors: Neil Bostrom, Millcreek, UT (US); Vance Scott Robinson, South Jordan, UT (US); Kasey Otho Greenland, West Jordan, UT (US); Santosh Ramachandran, Dublin, CA (US)

(73) Assignee: Varex Imaging Corporation, Salt Lake City, UT (US)

( * ) Notice: Subject to any disclaimer, the term of this patent is extended or adjusted under 35 U.S.C. 154(b) by 19 days.

(21) Appl. No.: 16/146,922

(22) Filed: Sep. 28, 2018

(51) Int. Cl.
*H01J 35/10* (2006.01)
*A61B 6/03* (2006.01)

(52) U.S. Cl.
CPC ............ *H01J 35/103* (2013.01); *A61B 6/032* (2013.01); *H01J 2235/1013* (2013.01); *H01J 2235/1026* (2013.01); *H01J 2235/1073* (2013.01)

(58) Field of Classification Search
CPC .............................. A61B 6/032; H01J 35/103; H01J 2235/1013; H01J 2235/1026; H01J 2235/1073
See application file for complete search history.

(56) References Cited

U.S. PATENT DOCUMENTS

| | | | |
|---|---|---|---|
| 4,504,965 A | 3/1985 | Ebersberger | |
| 6,198,803 B1 | 3/2001 | Osama et al. | |
| 6,327,340 B1 | 12/2001 | Runnoe | |
| 6,762,522 B2 | 7/2004 | Steinmeyer | |
| 7,203,280 B2 | 4/2007 | Anno et al. | |
| 7,206,380 B2 | 4/2007 | Anno et al. | |
| 8,385,505 B2 | 2/2013 | Coon et al. | |
| 2004/0080727 A1 | 4/2004 | Emoto | |
| 2010/0322383 A1* | 12/2010 | Coon | H01J 35/103 378/127 |
| 2015/0117604 A1 | 4/2015 | Chrost | |
| 2017/0301504 A1 | 10/2017 | Burke et al. | |

* cited by examiner

*Primary Examiner* — Mark R Gaworecki
(74) *Attorney, Agent, or Firm* — Maschoff Brennan

(57) ABSTRACT

In one example, a lift assembly may exert a force on a rotatable anode of an X-ray source. The lift assembly may include a lift shaft and a lift electromagnet. The lift shaft may be coupled to the anode and configured to rotate around an axis of rotation of the anode. The lift electromagnet may be configured to apply a magnetic force to the lift shaft in a radial direction. The lift electromagnet may include a curved surface that contours around at least a portion of the shaft wall. A radius of curvature of the curved surface of the lift electromagnet may be greater than a radius of curvature of the lift shaft, and the spacing between the curved surface of the lift electromagnet and the shaft wall may be non-uniform.

20 Claims, 19 Drawing Sheets

MAGNETIC ASSIST BEARING

BACKGROUND

The present disclosure generally relates to X-ray imaging systems, including embodiments relating to magnetic lift assemblies for X-ray sources used in X-ray imaging systems.

X-ray imaging systems typically include an X-ray source, a detector, and a support structure, such as a gantry, for the X-ray source and the detector. In operation, the X-ray source typically emits radiation, such as X-rays, toward an object. The radiation passes through the object and impinges on the detector. The detector receives the radiation and transmits data representative of the received radiation.

The X-ray source includes a cathode and an anode separated by a vacuum gap. X-rays are produced by applying an electrical current to an emitter of the cathode which emits electrons. The electrons accelerate towards and then impinge upon the anode. When the electrons impinge on the anode, some of the energy is converted to X-rays. The majority of the energy in the incident electron beam converts to heat in the anode. Because of high temperatures generated when the electron beam strikes the target, the anode can include features to distribute the heat generated, such as rotating a disc-shaped anode target. The disc-shaped anode target may be rotated by an induction motor via a bearing assembly.

The X-ray source and radiation detector can be components in an X-ray imaging system, such as a computed tomography (CT) system or scanner, which includes a gantry that rotates both the X-ray source and the detector to generate various images of the object at different angles. The gravitational (G) forces imposed by the rotation of the gantry and/or the rotation of the anode may result in stresses on components of the X-ray source. In particular, G forces resulting from the rotation of the gantry and/or the anode may result in stress on the bearing assembly of X-ray sources with rotating anodes. In addition, the stress on the bearing assembly may increase as rotation speeds increase, but increased rotation speeds may be desirable for high-performance X-ray sources and CT systems. The present disclosure includes solutions related to reducing the stresses on bearing assemblies in rotating X-ray imaging systems (e.g., CT scanners).

The subject matter claimed herein is not limited to embodiments that solve any disadvantages or that operate only in environments such as those described above. Rather, this background is only provided to illustrate one exemplary technology area where some embodiments described herein may be practiced.

DETAILED DESCRIPTION

Reference will be made to the drawings and specific language will be used to describe various aspects of the disclosure. Using the drawings and description in this manner should not be construed as limiting its scope. Additional aspects may be apparent in light of the disclosure, including the claims, or may be learned by practice.

The invention relates to reducing the loading on a bearing assembly of an anode assembly of an X-ray source using magnetics and, more particularly, to an electromagnet for lifting a shaft of the anode assembly to counter balance forces on the bearing assembly in a computed tomography (CT) system. The electromagnet may counter balance forces on the bearing assembly due to gantry rotation, anode rotation, gravity, etc. Example embodiments include a lift electromagnet (or magnetic actuator or lift magnet) in various positions relative to the anode and bearing assembly and various variations of the lift electromagnet and component to support magnetic lift on the bearing assembly in the anode assembly. In some circumstances, the magnetic lift may also be referred to as a magnetic assist bearing.

Reference will now be made to the drawings to describe various aspects of example embodiments of the disclosure. It is to be understood that the drawings are diagrammatic and schematic representations of such example embodiments, and are not limiting of the disclosure, nor are they necessarily drawn to scale.

Figure 1:
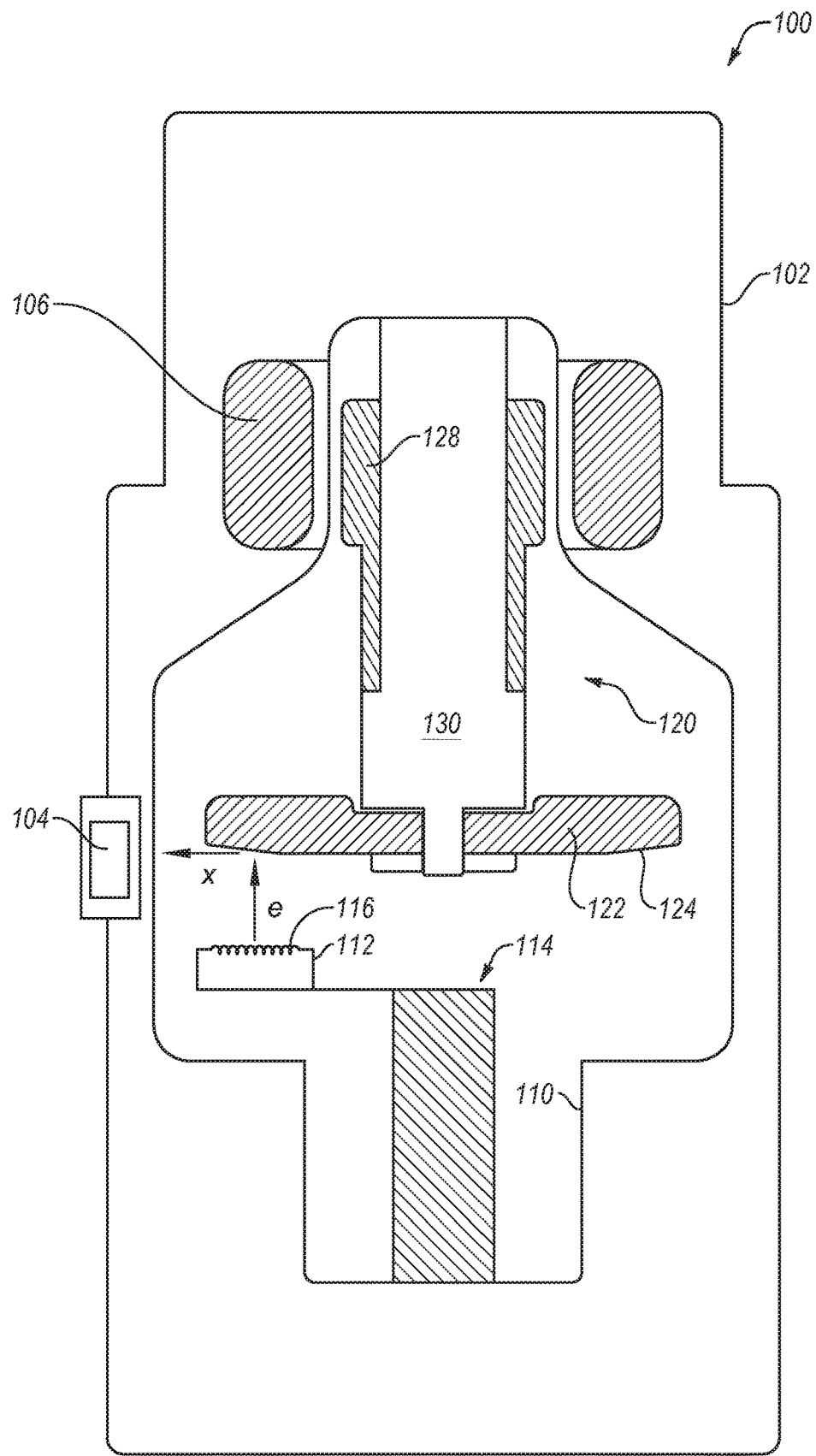
FIG. 1 illustrates a schematic diagram of an example X-ray source.

FIG. 1 is a schematic diagram of an example rotary or rotating anode X-ray source 100 with a rotatable disc-shaped anode 122. The X-ray source 100 includes a housing 102 and an X-ray insert 110 within the housing 102. The housing 102 encloses the insert 110. A fluid coolant such as a dielectric oil or air may fill the space or cavity between the housing 102 and the insert 110 to dissipate heat generated by the X-ray source 100.

A cathode 112 of a cathode assembly 114 and an anode assembly 120 are positioned within an evacuated enclosure (or vacuum envelope) defined by the insert 110. The anode assembly 120 includes the anode 122, a bearing assembly 130, and a rotor 128 mechanically coupled to the bearing assembly 130. The anode 122 is spaced apart from and oppositely disposed to the cathode 112. The anode 122 and cathode 112 are connected in an electrical circuit that allows for the application of a high voltage difference (or high electric potential) between the anode 122 and the cathode 112. The cathode 112 includes an electron emitter 116 that is connected to a power source.

Prior to operation of the X-ray source 100, the insert 110 may be evacuated to create a vacuum, which may be enclosed by the insert 110. During operation, heat and electrical potential is applied to the electron emitter 116 of the cathode 112 to cause electrons, denoted as "e" in FIG. 1, to be emitted from the cathode 112 by thermionic emission. The application of a high voltage differential between the anode 122 and the cathode 112 then causes the electrons "e" to accelerate from the electron emitter 116 toward a focal spot on a focal track 124 that is positioned on the anode 122. The focal track 124 may include, for example, a material having a high atomic ("high Z") number such as tungsten (W), rhenium (Re) or other suitable material. As the electrons "e" accelerate, they gain a substantial amount of kinetic energy, and upon striking the rotating focal track 124 some of this kinetic energy is converted into X-rays, denoted as "x" in FIG. 1.

The focal track 124 is oriented so that emitted X-rays "x" may travel through an X-ray source window 104. The window 104 includes an X-ray transmissive material, such as beryllium (Be), so the X-rays "x" emitted from the focal track 124 pass through the window 104 in order to strike an intended object and then a detector to produce an X-ray image.

As the electrons "e" strike the focal track 124, a significant amount of the kinetic energy of the electrons "e" results in heat, a large portion of which is transferred to the focal track 124, particularly in the region of the focal spot. To reduce the heat at a specific focal spot on the focal track 124, a disc-shaped anode target is rotated at high speeds, typically using an induction motor that includes a rotor 128 and a stator 106. The induction motor can be an alternating current (AC) electric motor in which the electric current in the rotor 128 needed to produce torque is obtained by electromagnetic coupling with the stator winding. The rotor 128 is mechanically coupled to the anode 122 through a hub of the bearing assembly 130 such that rotation of the rotor is transferred to the anode. In other configurations, the motor can be a direct current (DC) motor.

To avoid overheating the anode 122 from the heat generated by electrons "e", the rotor 128 rotates the anode 122 at a high rate of speed (e.g., 80-300 Hz) about a centerline of a shaft so that the region of the anode exposed to the beam of electrons "e" varies along the focal track 124. The X-ray source 100 can also include other cooling features to manage the heat generated by the anode 122 and the cathode 112.

An X-ray source (such as the X-ray source 100) and a radiation detector can be included in a rotational X-ray imaging system, such as a computed tomography (CT) scanner. CT involves the imaging of the internal structure of an object by collecting several projection images ("radiographic projections") in a single scan operation ("scan"), and is widely used in the medical field to view the internal structure of selected portions of the human body. Typically, several two-dimensional projections are made of the object, and a three-dimensional representation of the object is constructed from the projections using various tomographic reconstruction methods. From the three-dimensional image, conventional CT slices through the object can be generated. The two-dimensional projections are typically created by transmitting radiation from an X-ray source through the object and collecting the radiation onto a two-dimensional imaging device (i.e., radiation detector), or imager, which may include an array of pixel detectors (simply called "pixels"). One example of such a CT system is shown in FIG. 2A.

Figure 2A:
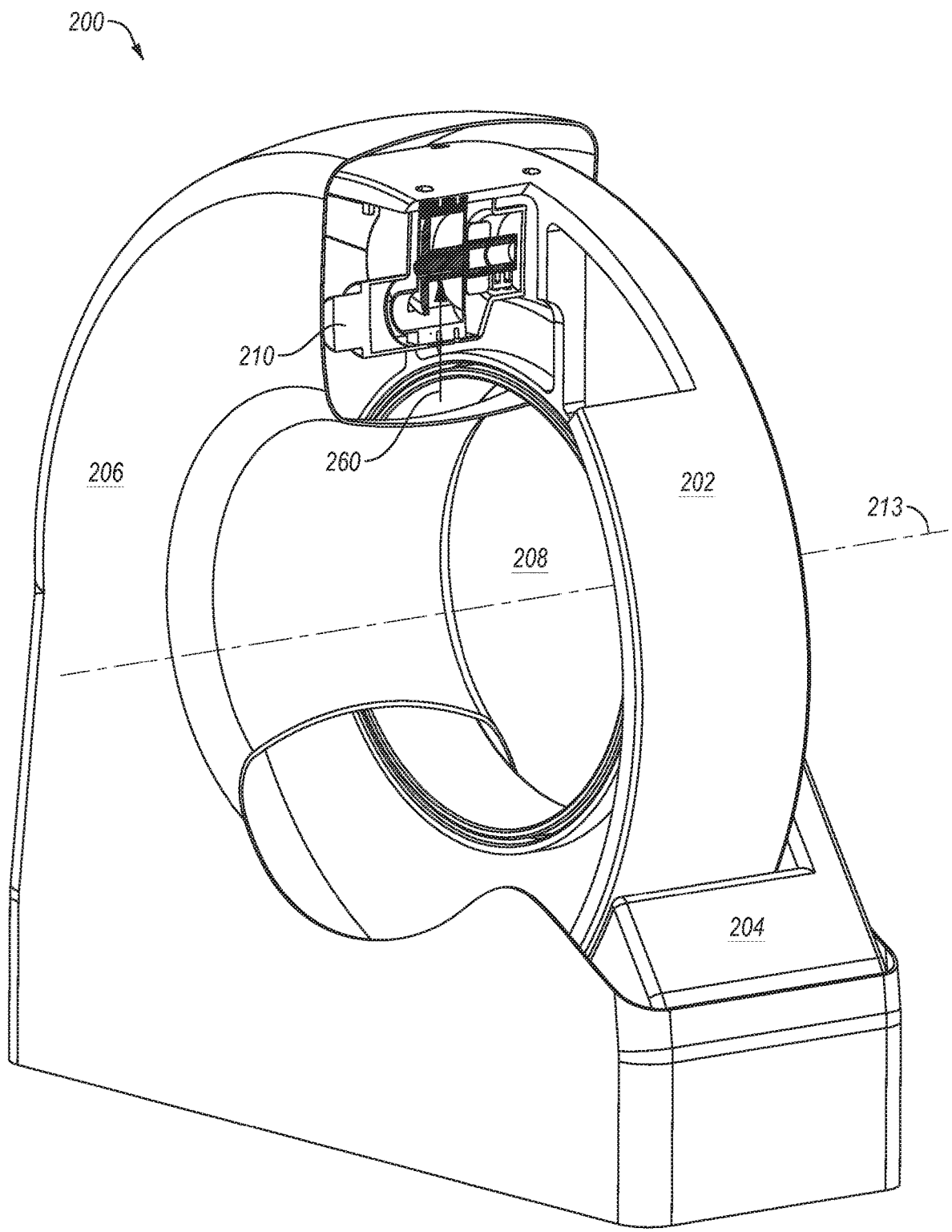
FIG. 2A illustrates a perspective view of an example gantry.

FIG. 2A illustrates an example of a gantry 200 of a rotating X-ray system. In some circumstances the gantry 200 may be referred to as a rotating assembly or a gantry assembly. The gantry 200 includes a stationary gantry frame 204 that supports a rotatable gantry frame 202. The rotatable gantry frame 202 may support an X-ray source 210 and a radiation detector or imager (not shown). The gantry 200 also includes a gantry cover 206 to enclose the rotating components and/or the stationary gantry frame 204 as well as provide an aesthetic covering.

The rotatable gantry frame 202 may include an annular shape (i.e., ring shape) that rotates about a center of axis in a gantry aperture 208 of the rotatable gantry frame 202. The centrifugal force (or gantry force), denoted via arrow 260, on components disposed on the rotatable gantry frame 202 may exceed a unit of gravitational force (g-force, G's, g's, or G loads), and may be a multiple of the g-force (e.g., 20 times the g-force). For example, components on the X-ray source 210, such as the bearing assembly, may experience a force of 37$g$'s if the X-ray source 210 is mounted on the rotatable gantry frame 202 at a radius of 0.7 meters from the center of axis and the rotatable gantry frame 202 is rotating at 0.275 seconds/rotation (sec/rot).

Generally, it is desirable for CT scanners to operate at higher rotational gantry speeds. However, operating CT scanners with gantries that rotate at higher speeds may adversely affect X-ray source bearing life because the bearing assemblies experience larger forces (e.g., g-forces from gantry rotation). In such circumstances, higher gantry speeds, and resultant centrifugal forces 260, can decrease the life of the bearing assembly.

Some X-ray sources implement liquid metal bearings (LMB), which may be capable of effectively handling higher forces (e.g., g-forces). However, implementing LMB can significantly increase costs and may require significant changes to the system design (e.g., the design of the X-ray source).

Other X-ray sources may implement magnetic lift configurations to magnetically assist in supporting the rotating components of the X-ray source and to decrease the forces on the bearing assembly. In some circumstances, such configurations may be advantageous over LMB because they may be implemented in existing imaging systems and/or they may provide very cost effective backwardly compatible improvements. With attention to FIG. 2B, an example of a magnetic lift configuration will be described in further detail.

Figure 2B:
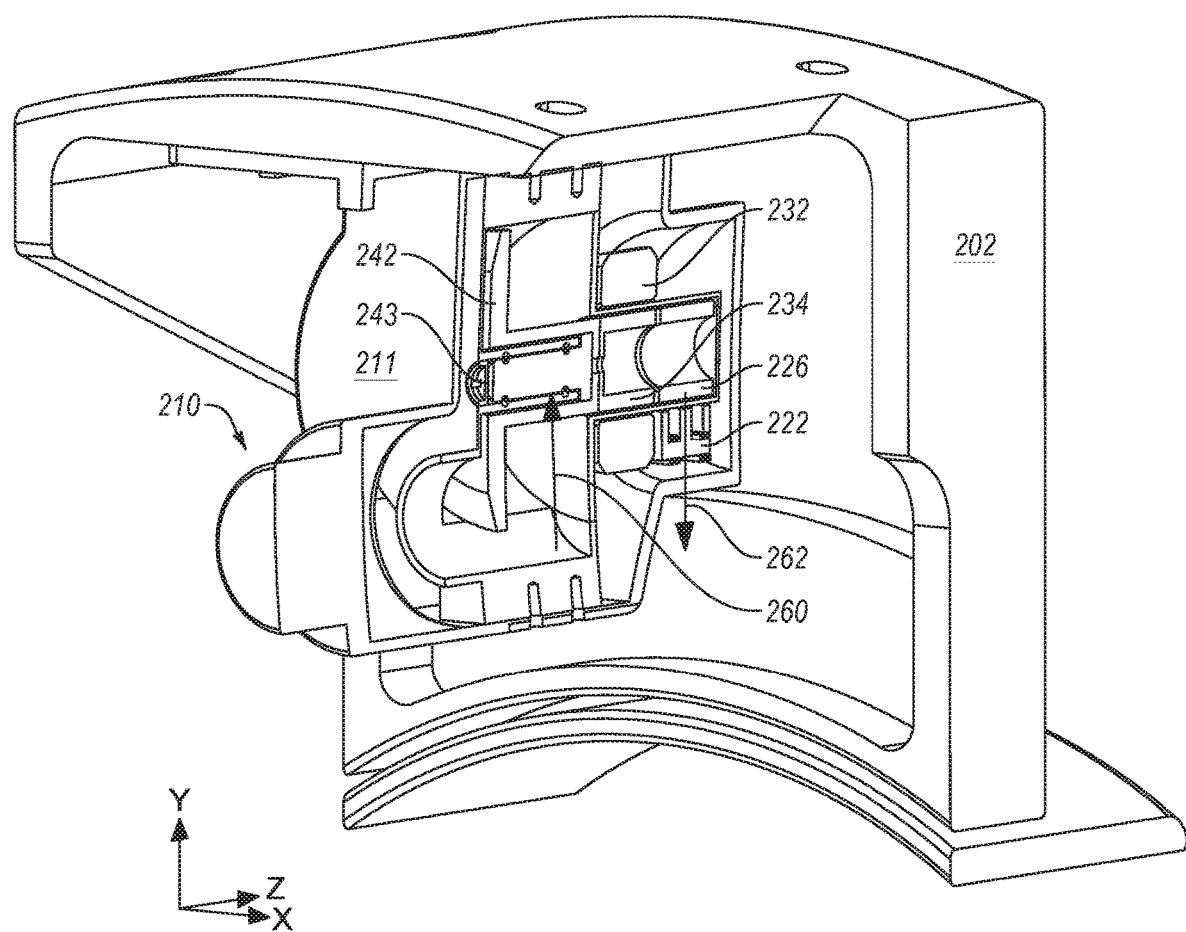
FIG. 2B illustrates a perspective view of a portion of the gantry of FIG. 2A that includes a rotating anode X-ray source.

FIG. 2B illustrates a portion of the gantry 200, and in particular, the X-ray source 210 attached to the rotatable gantry frame 202. The X-ray source 210 includes a source housing 211, an anode 242 that can receive electrons emitted by a cathode (112 of FIG. 1), a rotor 234 coupled to a shaft 243 of the anode 242, a stator 232 surrounding the rotor 234, a ferromagnetic lift shaft 226 coupled to the rotor 234, and a lift electromagnet 222 (or lift multipole electromagnet or electromagnet) that can provide a magnetic lift force, denoted via arrow 262, to the lift shaft 226 and thereby "lift" the rotor 234 and the shaft 243 of the anode 242 along the radial direction with respect to the axis of rotation of the gantry in opposition to the centrifugal force.

As used herein, lifting refers to an application of force along the radial direction of the lift shaft 226. The lifting or lift force can be an attractive force that pulls two components together (e.g., the lift shaft 226 and the lift electromagnet 222) or a repulsive or repelling force that pushes two components apart (e.g., the lift shaft 226 and the lift electromagnet 222). In this disclosure, reference will be made to the lifting or the lift force as an attractive force, but the lifting or the lift force can be a force with any magnitude (positive or negative) along the radial direction.

For descriptive purposes, FIG. 2B includes a Cartesian coordinate system with the y-axis in the vertical direction, the x-axis in the horizontal direction, and the z-axis orthogonal to the x-y plane. The rotation of the gantry 200 occurs in the x-y plane and the centerline of the shaft 243 of the anode 242 or the axis of rotation of the anode 242 extends parallel to the z-axis. During gantry rotation, a centrifugal force 260 is applied to the X-ray source 210 orthogonal-axis 213 of the gantry 200.

The lift electromagnet 222 may apply the magnetic lift force 262 (e.g., magnetic force, counter acting force, or balancing force) in substantially the opposite direction of the centrifugal force 260 so as to offset, dampen, reduce, or balance the forces (including the centrifugal force 260 of the gantry 200) on the bearing assembly or anode assembly. The magnetic lift force 262 may result in one or more of the following: reduce vibration or noise, increase bearing life, increase the bearing load capability, control thermal contact, improve the centering and precision of the rotating assembly, and allow the use of smaller bearings (e.g., ball bearings or other rotating bearings). Additionally or alternatively, the assistance of the magnetic lift force 262 may permit the use of other bearing types in a rotating anode X-ray source. In the case of medical imaging, reducing vibration and noise may also improve the patient's and/or medical staff's experience.

Figure 3A:
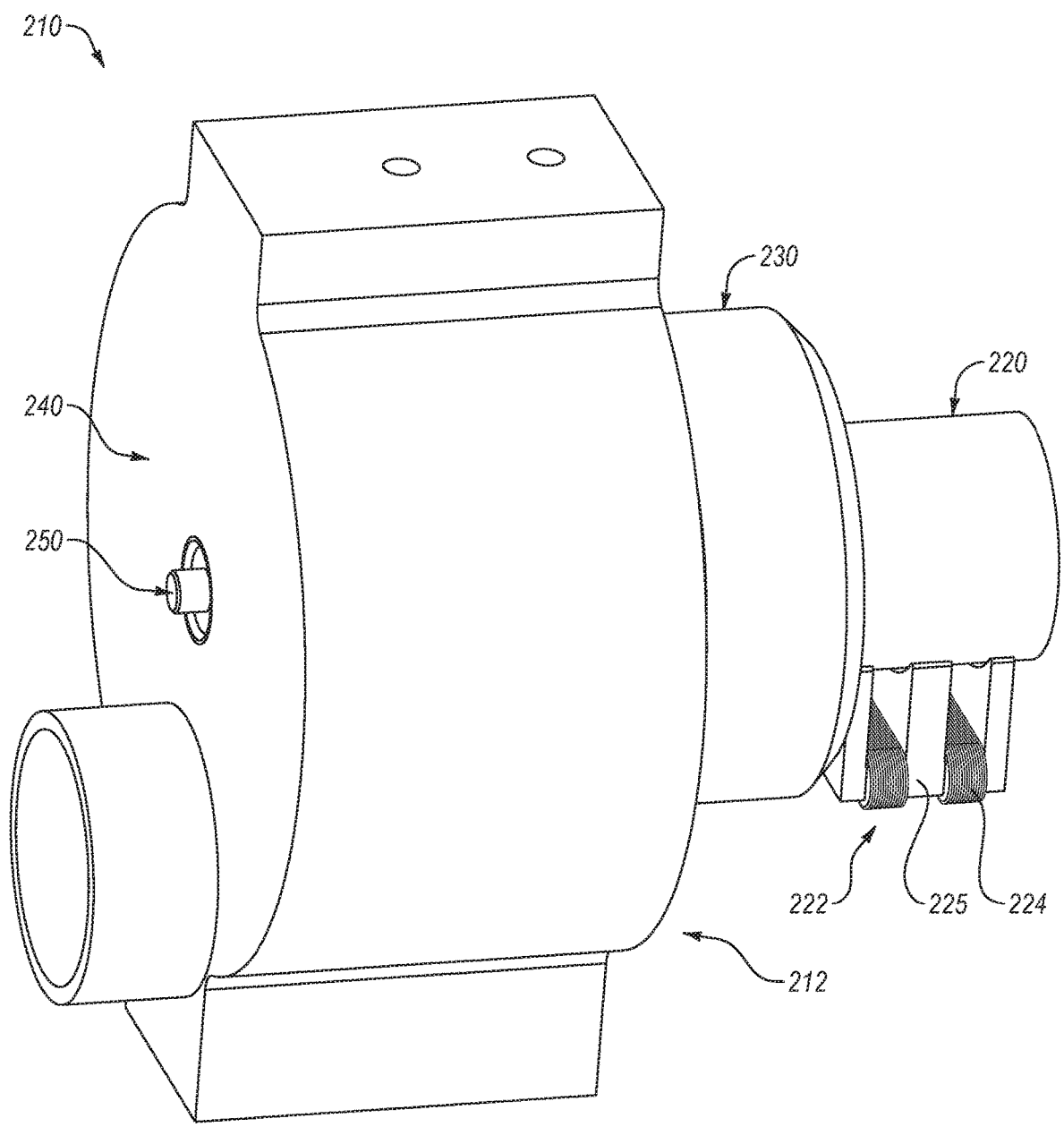
FIG. 3A illustrates a perspective view of another example of an X-ray source.

FIG. 3A illustrates a perspective view of the X-ray source 210. As shown in FIG. 3A, the X-ray source 210 may include an envelope, also referred to as an insert, 212 that includes a wall (e.g., insert wall, vacuum wall or vacuum envelope wall) that encloses the cathode and anode in an evacuated enclosure (or vacuum envelope). The insert 212 may enclose an anode assembly 240, a bearing assembly 250, a motor assembly 230 and a lift assembly 220. The lift electromagnet 222 may include a lift electromagnet core 225 with three poles formed in an "M" or "W" shape with windings (or coils or wires) 224 wrapped around the core 225 between the poles as shown, or around the poles.

Figure 3B:
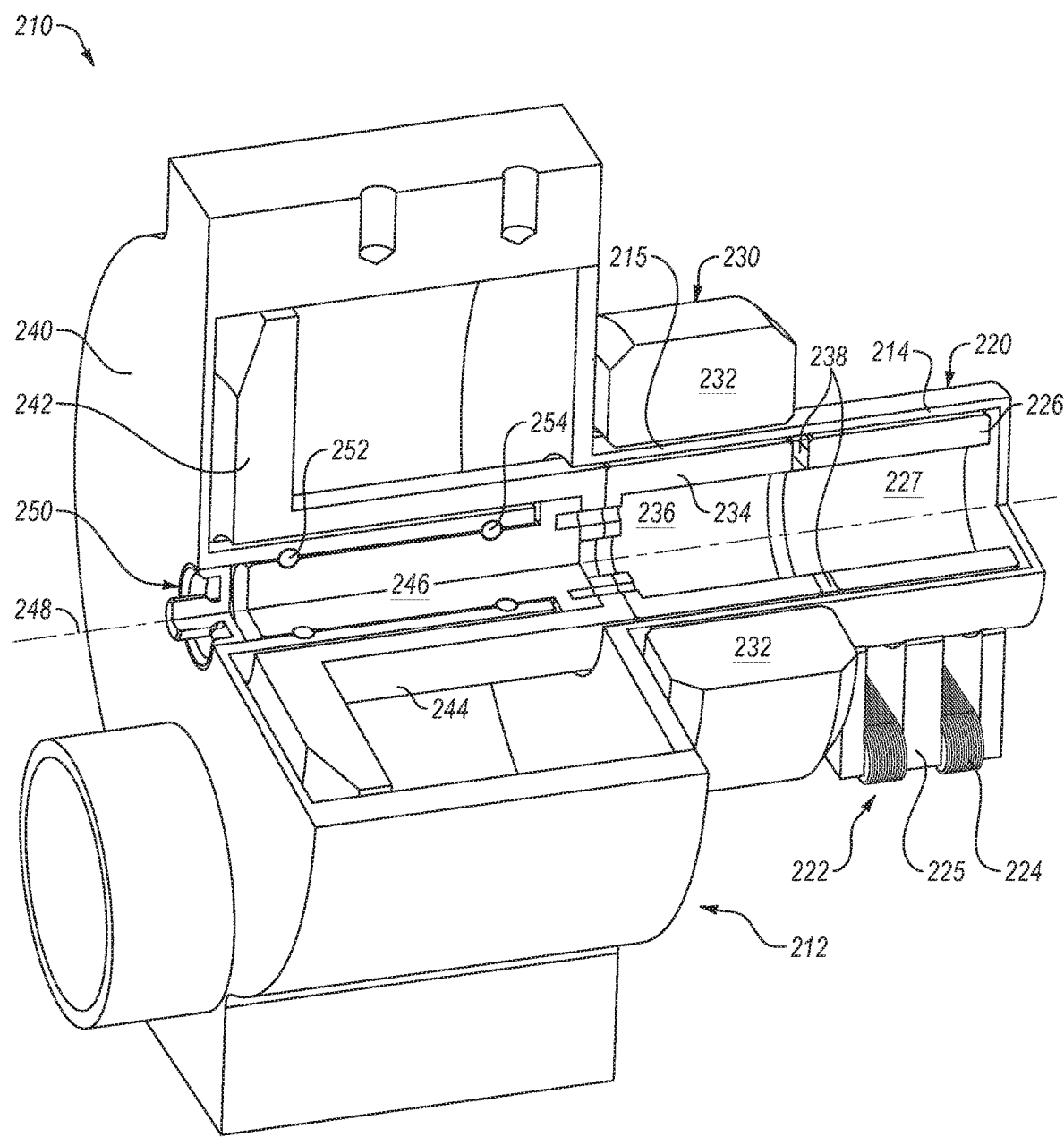
FIG. 3B illustrates a perspective section view of the X-ray source of FIG. 3A.
Figure 3C:
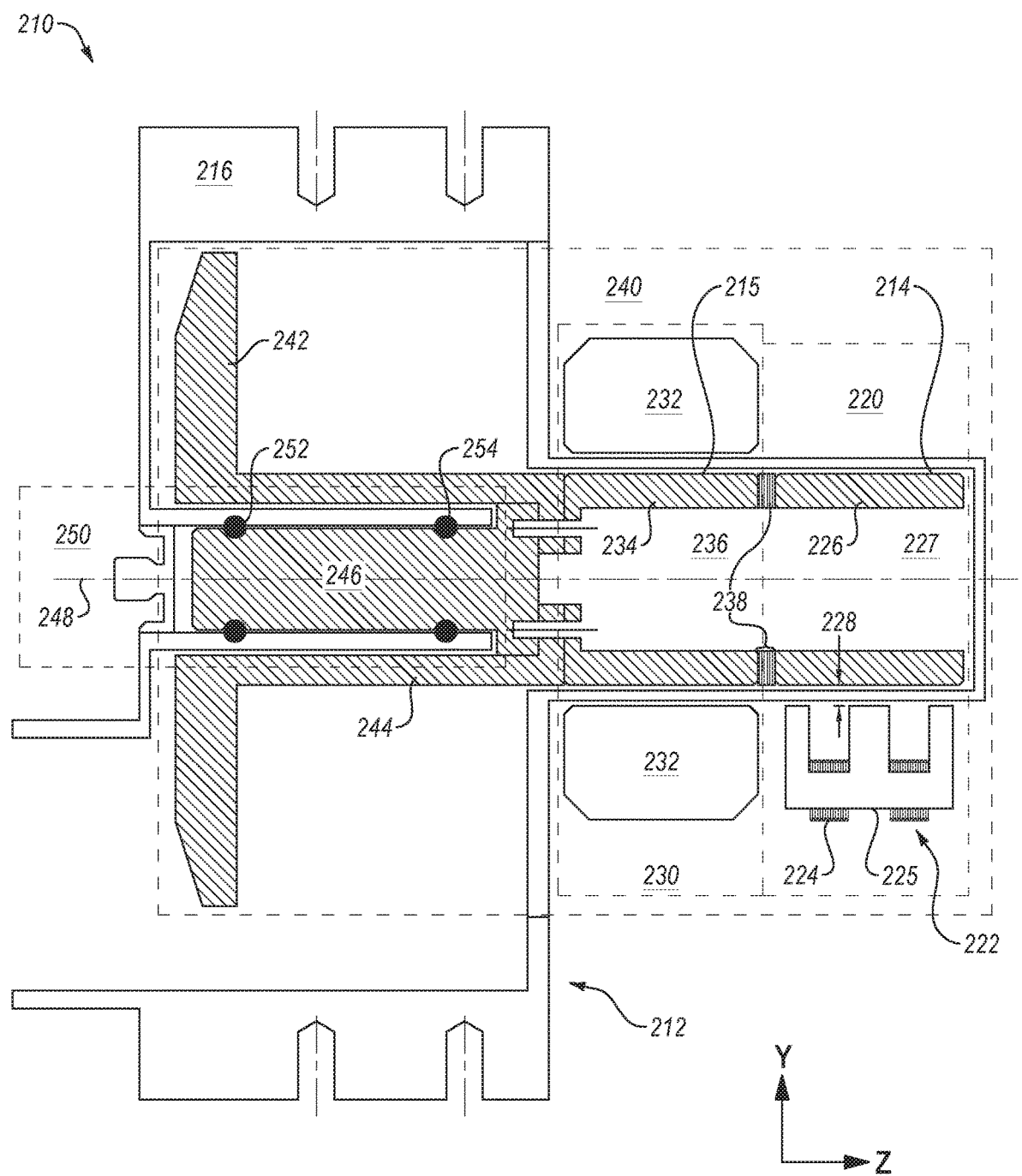
FIG. 3C illustrates a side cross section view of the X-ray source of FIG. 3A.

FIG. 3B illustrates a perspective section view of the X-ray source 210 and FIG. 3C illustrates a side cross section view of the X-ray source 210. As shown in FIGS. 3B-3C, the anode assembly 240, the bearing assembly 250, the motor assembly 230, and lift assembly 220 may facilitate rotation about an anode assembly centerline (or bearing centerline) 248. The anode assembly 240 includes an anode 242 and an anode outer shaft 244 that supports the anode 242. The anode assembly 240 also includes an anode inner shaft 246 that is coupled to the anode outer shaft 244 and rotatably coupled to the bearings 252 and 254 of the bearing assembly 250.

The anode inner shaft 246 may include at least one bearing race (e.g., ball bearing race). For example, in the illustrated configuration the bearing assembly 250 includes the outer ball bearing 252 and a corresponding race on the anode inner shaft 246, and an inner ball bearing 254 and a corresponding race. As used herein, outer refers to a relative position closer to an edge of the anode assembly 240, closer to the anode 242, or further away from the motor assembly 230. Inner refers to a position closer to a middle of the anode assembly 240, further away from the anode 242, or closer to the motor assembly 230.

Although the illustrated embodiment includes a roller element bearing (e.g., tool steel ball bearing or tool steel raceways), in other embodiments other bearing types may be implemented. For example, other configurations may include plain bearings (e.g., a sleeve bearing or a journal bearing), or hydrodynamic bearings, such as liquid metal bearings. U.S. patent application Ser. No. 14/968,078, filed Dec. 14, 2015, entitled, "Antiwetting Coating for Liquid Metal," which is hereby incorporated by reference in its entirety, discloses an example of a liquid metal bearing.

The motor assembly 230 may include a stator 232 and a rotor 234. The rotor 234 includes a rotor void 236 or opening on one end, which may be cylindrical. The rotor void 236 allows the rotor 234 to be attached to the anode shaft (e.g., the anode inner shaft 246) and/or aligned with the bearing centerline 248. The components (e.g., the anode shaft, the rotor 234, or the rotor shaft) may be attached to each other using a permanent or semi-permanent fastening or attachment mechanisms. An insert wall 215 (or a portion of the insert wall) proximate the motor assembly 230 may be disposed between the rotor 234 and the stator 232. The electromagnetic induction from the magnetic field of winding of the stator 232 may pass through the insert wall 215 to the rotor 234. A small gap between the insert wall 215 and the rotor 234 allows the rotor 234 to rotate without mechanical resistance.

The lift assembly 220 includes the lift shaft 226 coupled to the rotor 234 and the lift electromagnet 222 that may apply a magnetic force on the lift shaft 226. The lift shaft 226 may include a lift shaft void 227 or an opening, which may cylindrical. A rotor-to-lift shaft adapter 238 may couple the rotor 234 to the lift shaft 226. The rotor-to-lift shaft adapter 238 can include a non-ferromagnetic material to improve magnetic isolation between the motor assembly 230 and the lift assembly 220 which both use magnetic fields for operation. In non-illustrated configurations, the lift shaft 226 may be integrated with or permanently attached (e.g., welded or brazed) to the rotor 234.

The lift electromagnet 222 may include at least two poles that are oriented towards the lift shaft 226. In some configurations, the lift electromagnet 222 may include three poles (tri-pole) formed in an "M" or "W" shape with windings 224 wrapped around the core 225 (or a core web) between the poles.

Material choices may affect the performance of a magnetic device, such as the lift electromagnet 222 or the lift shaft 226. Magnetic material needs to stay magnetized in vacuum (e.g., the vacuum envelope of an X-ray source) and after processing and be vacuum compatible, such as cold drawn carbon magnetic iron (CMI-C).

The lift electromagnet 222 or the lift shaft 226 may include ferromagnetic and/or ferrimagnetic materials. As used herein and for simplicity in describing the technology, a "ferromagnetic" material refers to a material that can exhibit spontaneous magnetization (i.e., either a ferromagnetic material or a ferrimagnetic material).

The windings 224 around the core 225 may include an electrical conductive material (e.g., copper or aluminum) with an electrically insulated sheath, such as enameled magnet wire (i.e., transformer wire or Litz wire).

Two factors that can reduce the lift force between the lift shaft 226 and the lift electromagnet 222 are the size of the lift gap and the presence of interstitial materials such as the insert wall with magnetic permeability greater than 1. As shown in FIG. 3C, a lift gap 228 may be the spacing between the lift shaft 226 and the lift electromagnet 222. The lift gap 228 may include the insert wall 214 proximate the lift assembly 220 along with a vacuum between the insert wall 214 and the lift shaft 226. In some examples, the lift gap 228 may include the space between the insert wall 214 and the lift electromagnet 222 when the lift electromagnet 222 does not touch the insert wall 214, such as when the lift electromagnet 222 and the insert wall 214 have different electrical potentials. The lift gap 228 that includes the vacuum provides clearance for the lift shaft 226 to rotate without mechanical resistance (e.g., friction from touching the insert wall 214 or the lift electromagnet 222).

Vacuum and air have a relative magnetic permeability (represented by $\mu_r$), of 1, thus they don't dampen the electromagnetic coupling between the electromagnet shaft 226 and the lift electromagnet 222. The insert wall 214 is typically made of a conductive material with a magnetic permeability >1 such that it can dampen the electromagnetic coupling between the lift electromagnet 222 and the lift shaft 226 reducing the lift force.

Magnetic permeability is the measure of a material's ability to support the formation of a magnetic field within itself. Relative magnetic permeability is the ratio of the magnetic permeability of a given material to that of free space. Reducing the thickness of the insert wall 214 and/or using materials with low relative magnetic permeability will ensure that damping of the magnetic force generated between the lift electromagnetic 222 and the electromagnet shaft 226 is minimized. The insert wall 214 in the lift region may include materials with a low magnetic permeability or minimal ferromagnetic properties, such as stainless steel. Additionally, reducing the lift gap 228 may increase the magnetic force applied to the lift shaft 226 by the lift electromagnet 222. The force of the lift electromagnet 222 on the lift shaft 226 is inversely proportional to the square of the lift gap, which force F can be approximated at low fields by the simplified formula $F=1/gap^2$, where the lift gap 228 is represented by gap. In one example, the lift gap 228 may be less than 2 millimeters (mm). In another example, the lift gap 228 may be less than 1 mm.

For the magnetic flux of the magnetic field to primarily act on the lift shaft 226 instead of between poles, the distance between pole ends may be at least ten times greater than the lift gap 228. In an example, the insert wall 214 in the lift region may be less than 1 mm.

The lift assembly 220 may apply a magnetic lift force on the rotating assembly (via the lift shaft 226), which can, for example, improve the operating lifespan and/or increase the load bearing capability of the bearing assembly 250 and components thereof. The magnetic force of the lift electromagnet 222 may be used to counteract loads on the bearing assembly 250, such as the centrifugal force of the gantry (e.g., the gantry 200), as well as to dampen vibration and add stability to the anode assembly (e.g. anode assembly 240) or other rotating components of the X-ray source. The forces generated by the lift assembly 220 may be applied anywhere on the rotating assembly including at the center or mass (or not at the center of mass) and may employ one or a combination of magnetic lift devices that provide the forces.

The X-ray source 210 may include any suitable features described in U.S. patent application Ser. No. 15/464,142, filed Mar. 20, 2017, entitled, "Magnetic Lift Device for an X-Ray Tube," which is incorporated herein by reference in its entirety. In particular, the X-ray source 210 may include any suitable aspects of the lift assemblies described in the above-referenced application, or any other suitable features.

As mentioned, a lifting force applied to a lift shaft by a lift electromagnet may counter balance forces on a bearing assembly and/or a rotating anode coupled to the lift shaft. For example, the lift force may counter balance static forces such as that caused by a gantry of a CT system that is constant for a given gantry rotation speed, and/or other dynamic forces that vary at frequencies equal to or higher than the rotation frequency of the rotating anode assembly. The lift electromagnet may be required to provide a sufficient controllable lifting force to the lift shaft rotating in a vacuum. Accordingly, disclosed embodiments include configurations to maximize the cross-sectional area of the lift electromagnet to generate a sufficient lift force. In addition, disclosed embodiments include configurations to maximize the coil density and efficiency of the arrangement of the windings around a core of the lift electromagnet, thereby reducing the electrical current required for lifting, increasing the lifting force, and/or directing the magnetic field to be exerted on the lift shaft.

Increasing the size of the lift electromagnet and/or the lift shaft lift may increase the lifting force generated by a lift assembly. However, the lift electromagnet and the lift shaft may need to fit in a certain size insert, evacuated envelope, and/or housing to be implemented in certain X-ray sources. Accordingly, the lift electromagnet and the lift shaft should be maximized within the constraints of the insert, evacuated envelope, and/or housing. Thus, disclosed embodiments include relatively compact designs that may be implemented in various X-ray sources. In addition, since the lift shaft is coupled to and rotates with the anode and/or the bearing assembly, it may be desirable in some applications to minimize the mass of the lift shaft (and therefore the rotating mass coupled to the anode and/or the bearing assembly). Accordingly, disclosed configurations may facilitate minimizing the mass of the lift shaft and/or the rotating assembly. Disclosed configurations of the lift electromagnet and the lift shaft permit the rotating assembly (the anode, the bearing assembly and the lift shaft) to rotate freely and minimize rotational drag. In addition, in order to operate effectively, the lift electromagnet and the lift shaft should be balanced so that one does not saturate before the other. Accordingly, the lift shaft size and electromagnetic size should have similar saturation maximums (e.g., should to be balanced).

Generally, magnetic fields surround and are created by magnetized material and by moving electric charges (electric currents) such as those used in electromagnets. The magnetic field may be represented by two distinct but closely related fields denoted by the symbols B and H. H field is typically measured in units of amperes per meter and B field is typically measured in teslas or newtons per meter per ampere. Saturation is the state reached when an increase in applied external magnetic H field cannot increase the total magnetic flux density B of the material further, so. Saturation is a characteristic of ferromagnetic and ferrimagnetic materials, such as iron, nickel, cobalt and their alloys.

In some configurations, lift electromagnets may operate in a partially or nearly complete saturation levels. Accordingly, it may be desirable to design lift electromagnets such that various portions of the lift electromagnet saturate at a similar power level. Thus, disclosed embodiments include configurations such that certain parts of the lift electromagnet saturate at a similar power level.

Figure 3D:
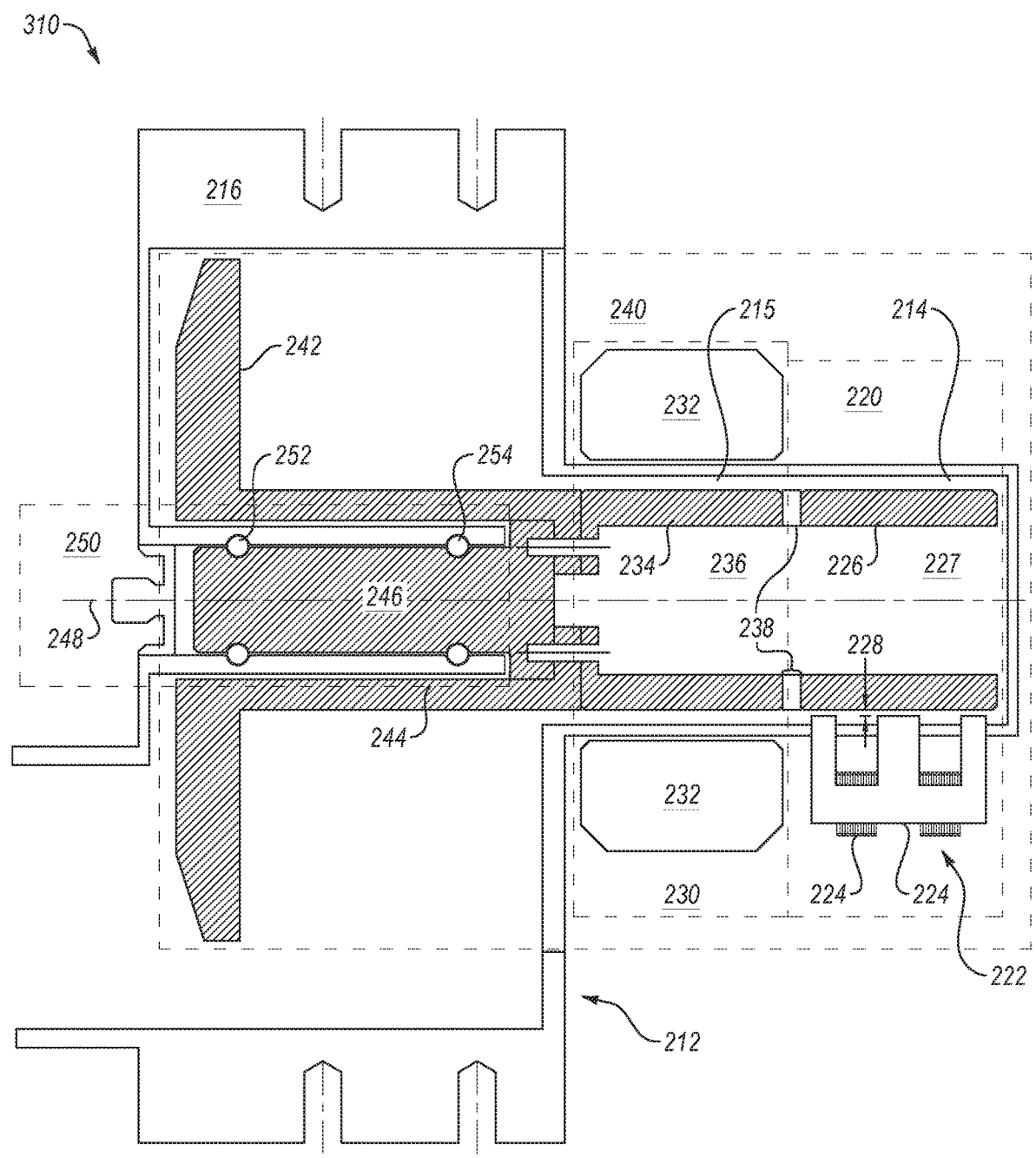
FIG. 3D illustrates a side cross section view of another example of an X-ray source.
Figure 3E:
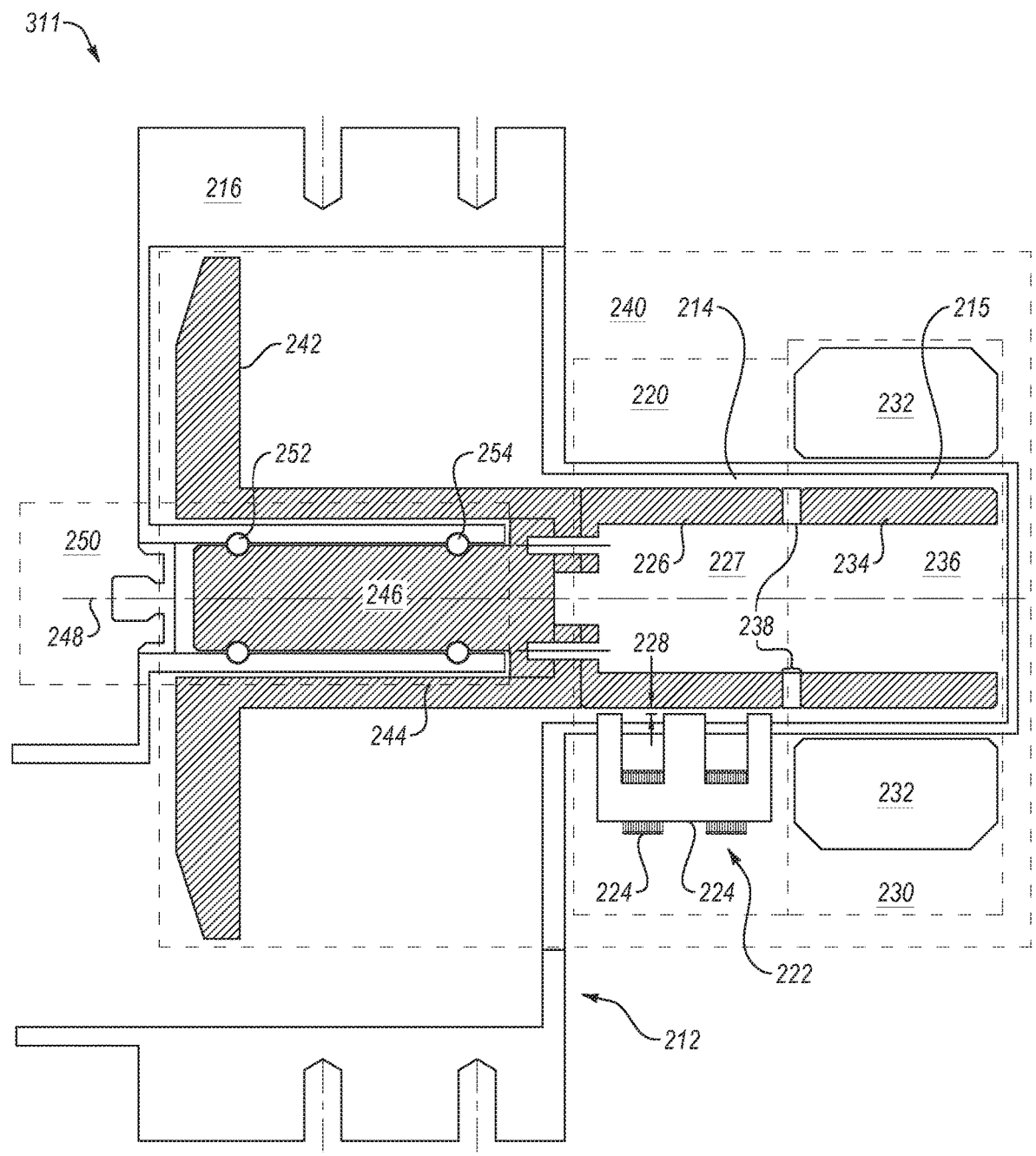
FIG. 3E illustrates a side cross section view of another example of an X-ray source.
Figure 4A:
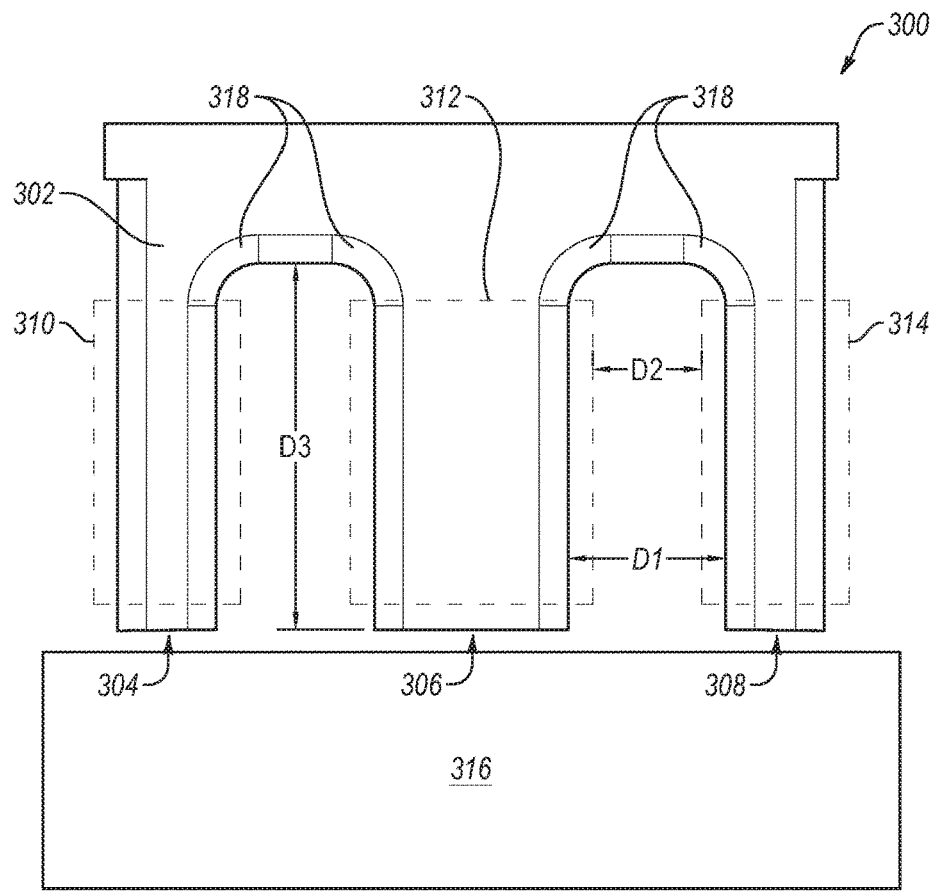
FIG. 4A illustrates a side view of an example of a lift electromagnet that be implemented in an X-ray source.

FIG. 4A illustrates a side view of an example of a lift electromagnet 300. The lift electromagnet 300 may include suitable aspects described with respect to the lift electromagnet 222 of FIG. 3C, such as a core 302 and with three poles 304, 306, 308. Windings 310, 312, and 314 may be wrapped around the core 302 between the poles 304, 306, 308. In FIG. 3D, the windings 310, 312, and 314 are indicated in dashed lines to better illustrate the lift electromagnet 300. The windings 310, 312, 314 may include an electrical conductive material (e.g., copper, aluminum or another suitable conductive material) with an electrically insulated sheath, such as an enamel or a polymer (e.g., polymide, or another suitable insulating material). As shown, the lift electromagnet 300 may be positioned proximate a lift shaft 316, to exert a lifting force on the lift shaft 316.

Although in the illustrated configuration the poles 304, 306, 308 are shown as a single component, in other configurations the poles 304, 306, 308 may be formed of separate pieces coupled to one another to form the poles 304, 306, 308. Such configurations are disclosed, for example, in U.S. patent application Ser. No. 16/146,867, filed Sep. 28, 2018, entitled, "Vacuum Penetration for Magnetic Assist Bearing," which is incorporated herein by reference in its entirety.

The lift electromagnet 300 may generate a B field that extends down the poles 304, 308 on the ends of the lift electromagnet 300 and up the pole 306 in the center of the lift electromagnet 300. The lift electromagnet 300 may be configured such that the B field is saturated in the poles 304, 306, 308 but is not saturated in the remaining portions of the core 302 of the lift electromagnet 300. When the B field is saturated in the poles 304, 306, 308, the poles 304, 306, 308 may be less sensitive to fluctuations in gap size or electrical current. The lift electromagnet 300 may include curved portions 318 positioned in between the poles 304, 306, 308. In particular, the curved portions 318 may be positioned on an end of the poles 304, 306, 308 opposite the lift shaft 316. The curved portions 318 may be configured to avoid magnetic saturation in the rest of the core 302 opposite the poles 304, 306, 308. In some configuration, the radius of curvature (or outside diameter) of the curved portions 318 may be selected to avoid magnetic saturation in the core 302. In contrast, sharp corners concentrate the magnetic field which may result in poles that experience magnetic saturation more readily.

The poles 304, 306, 308 may be spaced apart from one another a distance D1. The distance D1 may be selected to be sufficiently large enough to permit space for the windings 310, 312, 314. The windings 310, 312, 314 may be spaced apart from one another a distance D2. In some aspects, the distance D2 may be sufficiently small enough such that the windings 310, 312, 314 do not overlap with one another. However, in some configurations the distance D2 may be sufficiently large enough to avoid dielectric breakdown between the windings 310, 312, 314 (e.g., where electric current passes in between adjacent windings 310, 312, 314). In other configurations, a dielectric material may be added in between the windings 310, 312, 314 to avoid dielectric breakdown. In other aspects, it may be desirable to maximize the number of windings 310, 312, 314 that fit in between the poles 304, 306, 308 (e.g., distance D1) while minimizing the resistance of current traveling through the windings 310, 312, 314. In other aspects, it may be desirable to match the resistance of the windings 310, 312, 314 to the maximum volt and current output of the power supply to reduce the cost of the power supply or the windings 310, 312, 314.

The poles 304, 306, 308 may extend a distance D3 from the main portion of the core 302. The distance D3 may be large enough to permit a sufficient number of the windings 310, 312, 314 to be wound or positioned around the poles 304, 306, 308 to generate the magnetic field. At interfaces between the winding portion of the core and the coupling portion, it also serves to contain the magnetic field and direct it to the lift shaft 316. However, the distance D3 may be limited by design constraints of the lift electromagnet 300 and/or an X-ray source incorporating the lift electromagnetic. In particular, in some circumstances the size and mass of the X-ray source may constrain the maximum size and mass of the lift electromagnet 300 incorporated therein, and may therefore limit the size of the distance D3. However, the distance D3 may be maximized within those constraints.

In some configurations, the materials of the core 302 may be selected to maximize magnetic permeability and saturation in the poles 304, 306, 308. However, some materials with improved magnetic permeability may be expensive and cost-prohibitive to be included in lift electromagnets for X-ray sources. Accordingly, the core 302 material may be selected to maximize magnetic permeability and saturation without using a material that is cost-prohibitive.

For example, the core 302 material may include: annealed amorphous metal alloy with a relative maximum permeability of 1000000 ($\mu/\mu0$), iron (FE) annealed in hydrogen (H) with a relative maximum permeability of 200000, magnetic nanocrystalline alloy with a relative maximum permeability of 80000, mu-metal with a relative maximum permeability of 20000 or 50000, cobalt iron alloy with a relative maximum permeability of 18000, nickel-iron magnetic alloy (e.g., Permalloy) with a relative maximum permeability of 8000, iron (FE) with a relative maximum permeability of 5000, electrical steel with a relative maximum permeability of 4000, annealed ferritic stainless steel with a relative maximum permeability of 1000-1800 or other suitable materials.

Figure 4B:
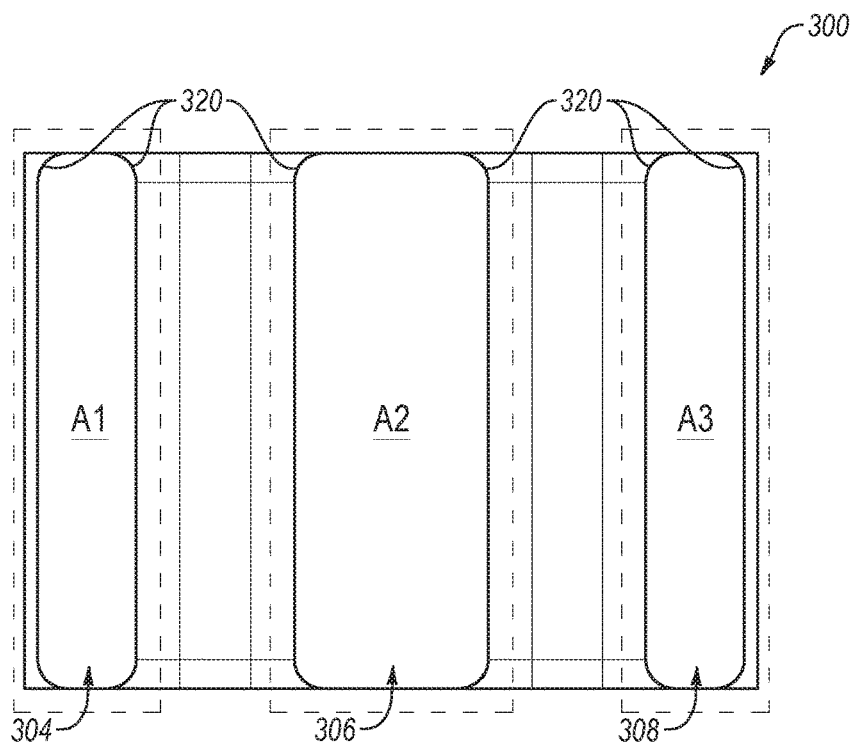
FIG. 4B illustrates a bottom section view of the lift electromagnet of FIG. 4A.

FIG. 4B illustrates a bottom section view of the lift electromagnet 300. As illustrated, the pole 304 includes an area A1, the pole 306 includes an area A2, and the pole 308 include an area A3. The areas A1, A2, and A3 may be configured to maximize the magnetic field in the lift electromagnet 300. In one example, the areas A1 and A3 may be substantially the same size, and the area A2 may be at least one and a half (1½), one and three quarters (1¾) or two (2) times the size of the area A1 or the area A3. In another example, the area A2 may be substantially the same size as the area A1 and A3 added together.

In other configurations, the area A2 may be slightly larger than two times the area A1 or the area A3. For example, the area A2 may be between 1%-5% larger than two times the area A1 or the area A3. In another example, the area A2 may be between 1%-100% larger than two times the area A1 or the area A3. In yet another example, the area A2 may be between 1%-5% larger than the area A1 and A3 added together. In a further example, the area A2 may be between 1%-100% larger than the area A1 and A3 added together.

The cross section or the areas A1, A2, A3 of the poles 304, 306, 308 may be substantially the same throughout the extent of the poles 304, 306, 308. Such configurations may result in a B field that is saturated at the poles 304, 306, 308 and not saturated in the remainder of the core 302.

In some configurations, the areas A1, A2, A3 may be maximized within the design constraints of the lift electromagnet 300 and/or an X-ray source incorporating the lift electromagnetic. In particular, in some circumstances the size of the X-ray source may constrain the maximum size of the lift electromagnet 300 incorporated therein. However, the areas A1, A2, A3 of the poles 304, 306, 308 may be maximized within those constraints.

The poles 304, 306, 308 may include rounded portions 320 (only some of which are labeled in FIG. 4B). The rounded portions 320 may facilitate winding the windings 310, 312, 314 around the poles 304, 306, 308. In particular, the radius of curvature of the rounded portions 320 may be selected not to exceed the internal radius of curvature of the windings 310, 312, 314. Such configurations may permit the windings 310, 312, 314 to be positioned close to or fully against the surface of the poles 304, 306, 308, in a space efficient manner. Additionally or alternatively, such configurations may facilitate in avoiding magnetic saturation in the poles 304, 306, 308. In some circumstances, the radius of curvature of the windings 310, 312, 314 may be limited by the material properties of the windings 310, 312, 314.

Figure 5A:
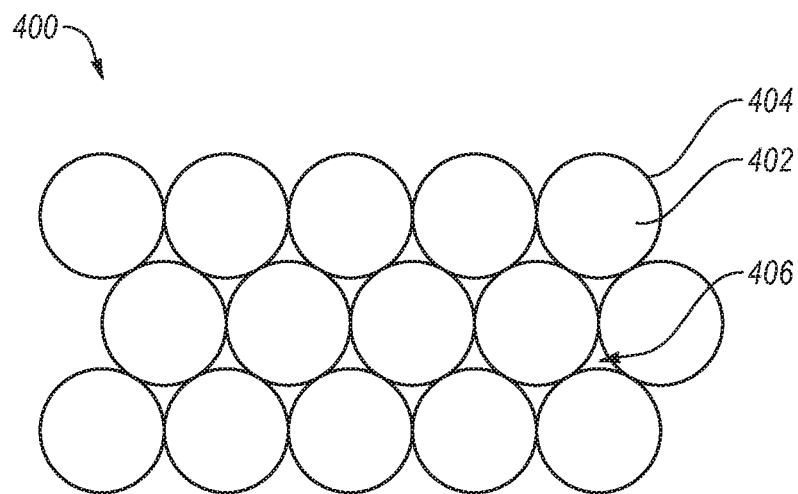
FIGS. 5A-5C illustrate section views of example embodiments of windings that may be implemented in lift electromagnets.
Figure 5B:
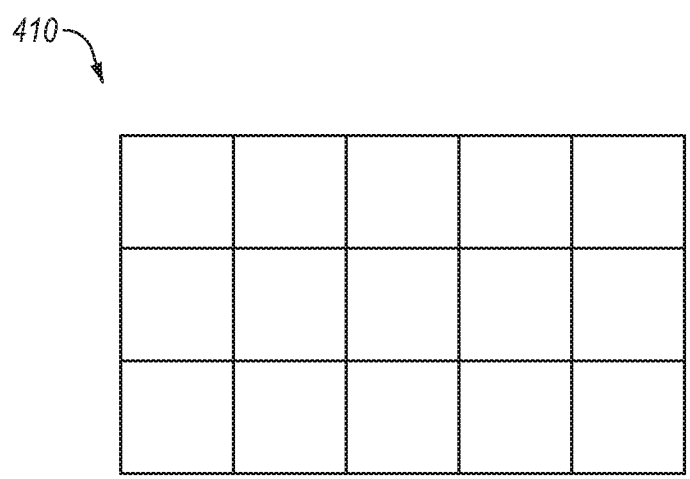
Figure 5C:
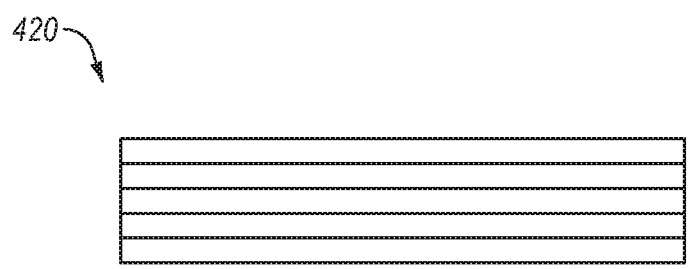

FIGS. 5A-5C illustrate section views of example embodiments of windings 400, 410, 420. As illustrated in FIG. 5A, the windings 400 may include an electrical conductive material 402 (e.g., copper or aluminum) surrounded by an electrically insulated sheath 404 (e.g., polymer or polyamide). In some configurations, the windings 400 may be formed of an insulated wire.

As shown in FIG. 5A, the windings 400 include a substantially circular or ellipse cross section. In contrast, the windings 410 of FIG. 5B include a square or rectangular cross section, and the windings 420 of FIG. 5C include a substantially planar or high aspect ratio rectangular cross section. As shown in FIG. 5A, even when the windings 400 are positioned close to one another, spaces 406 are included in between the windings 400. However, the windings 410 with the square cross section do not include the spaces 406 because of their shape, resulting in a relatively higher density of the windings 410 in a given volume (e.g., the space around the poles). Similarly, the windings 420 with the planar cross do not include the spaces 406 because of their shape, resulting in a relatively higher density of the windings 420.

In some configurations, the windings 420 may be formed of conductive foil. In such configurations, the layers of foil may need to be relatively thin to achieve the same cross-sectional area as other types of windings.

It may be desirable to maximize the total cross-sectional area of the windings in order to maximize the B field generated through the poles. Accordingly, the windings may be positioned around the poles in a manner to avoid spaces in between one another.

Figure 6:
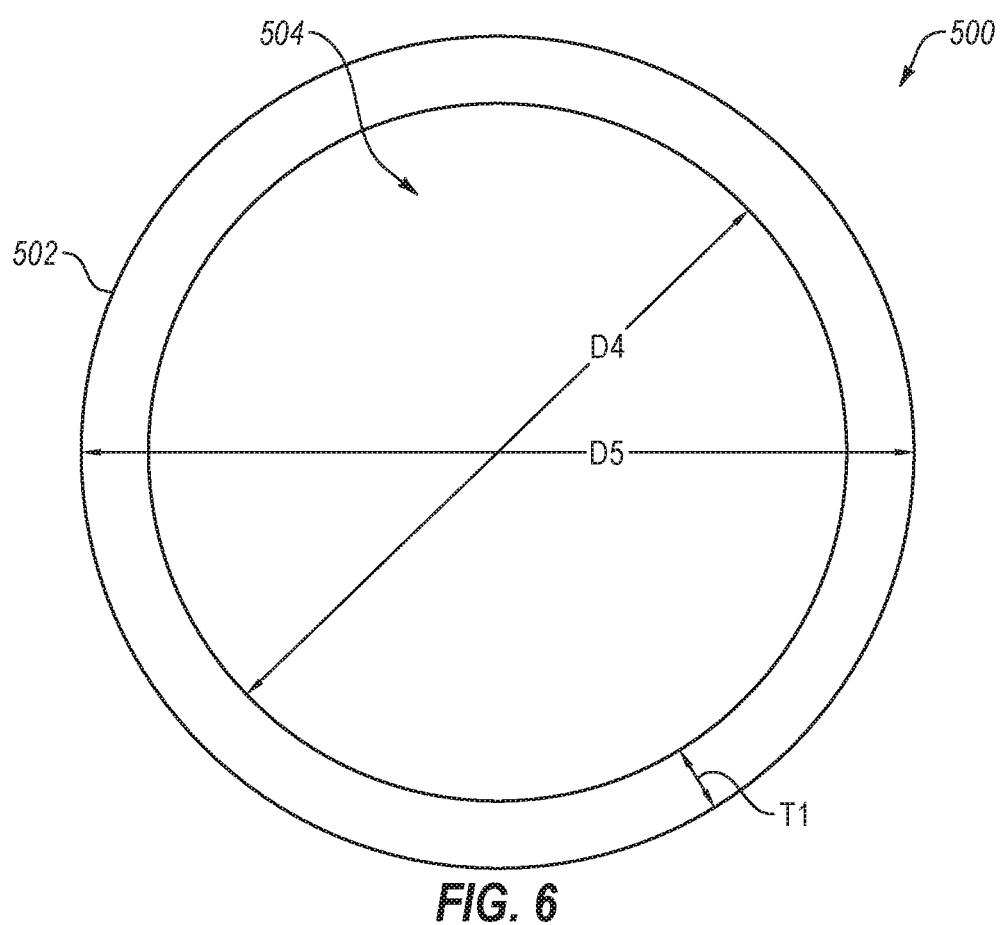
FIG. 6 illustrates a schematic section view of an example embodiment of a lift shaft that may be implemented in lift electromagnets.

FIG. 6 illustrates a schematic section view of an example embodiment of a lift shaft 500. The lift shaft 500 may be substantially cylindrical, with a shaft wall 502 with an annular cross-section. The shaft wall 502 may define an opening 504, and may include an inner diameter D4 and an outer diameter D5. A thickness T1 of the shaft wall 502 may depend on the inner diameter D4 and the outer diameter D5. The inner diameter D4 and the outer diameter D5 may be optimized such that the shaft wall 502 includes a desired thickness T1. In particular, the thickness T1 may be selected to minimize the rotating mass of the lift shaft 500, while maintaining suitable saturation through the shaft wall 502 and thus a suitable magnetic field through the lift shaft 500.

In some configurations, the thickness T1 of the shaft wall 502 may be minimized to reduce the rotating mass of the lift shaft 500. However, a minimal value of the thickness T1 may be selected such that the shaft wall 502 remains saturated to maximize the B field through the lift shaft 500 and to reduce the sensitivity of the applied force to variation in B field. Accordingly, the thickness T1 of the shaft wall 502 may be selected to correspond to this minimum value, thereby reducing the rotating mass and resulting in desirable magnetic performance.

Figure 7:
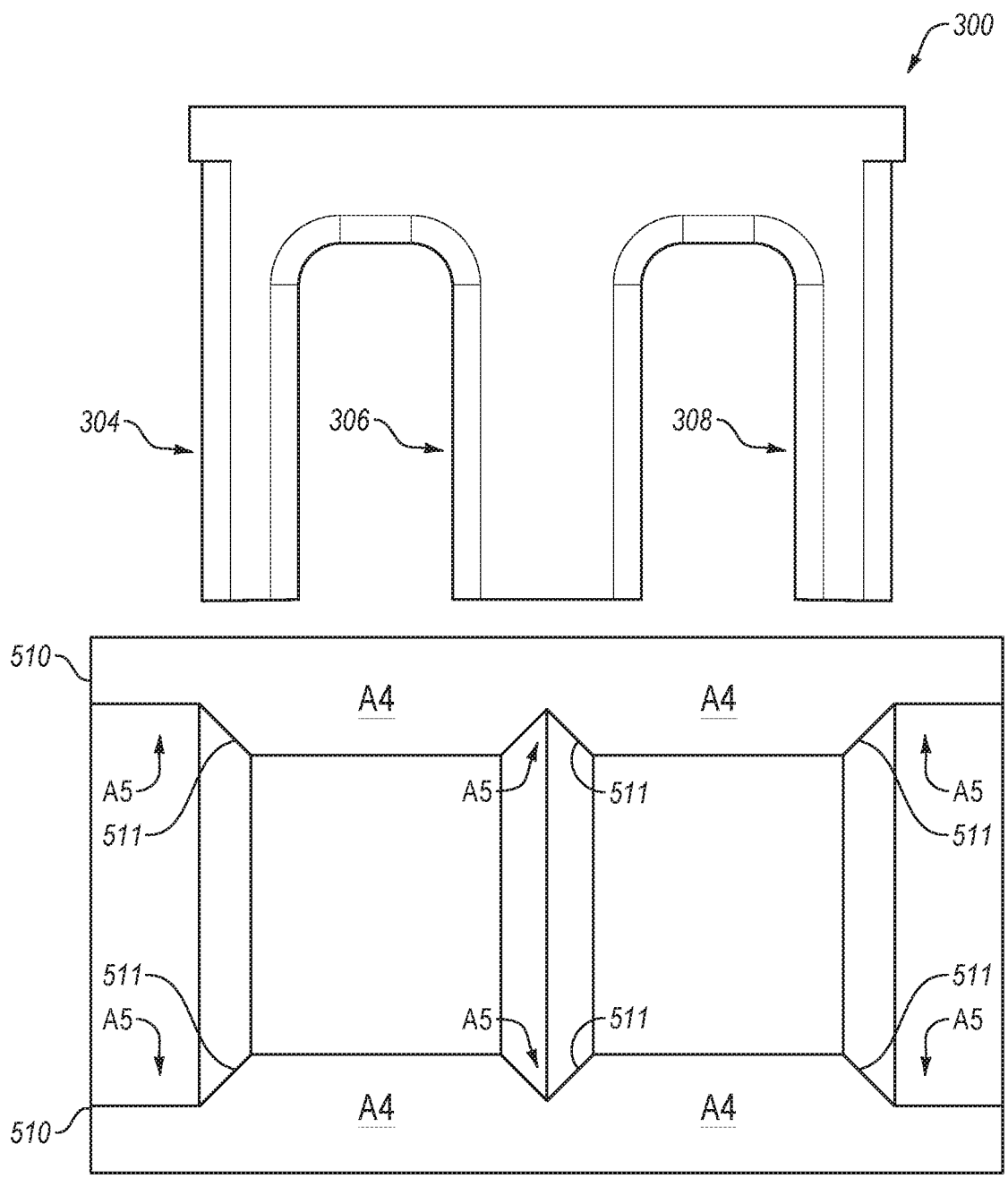
FIG. 7 illustrates a schematic view of an example embodiment of a shaft wall that may be implemented in a lift shaft.

FIG. 7 illustrates a schematic view of the lift electromagnet 300 positioned proximate an example embodiment of a shaft wall 510. The B field generated by the lift electromagnet 300 may travel down through the poles 304, 306, then through the shaft wall 510, and up through the pole 306. Generally the B field may extend through an area A4, denoted by dashed lines. Areas A5 surrounding the area A4 may have relatively low B field. Accordingly, in some embodiments, the volume of the shaft wall 510 with low B field, corresponding to the areas A5, may be reduced. In some configurations, the shaft wall 510 in the areas A5 may be minimized to reduce the rotating mass of a lift shaft (e.g., the lift shaft 500) incorporating the shaft wall 510 while still preserving structural integrity for the entire anode rotating assembly. The areas A5 of the shaft wall 510 may be reduced, for example, by machining or other suitable processes.

Accordingly, the shaft wall 510 may have a non-uniform thickness. In particular, in some configurations the shaft wall 510 may be thicker where the B field is stronger in between the poles 304, 306 and in between the poles 308, 306, and thinner on the ends of the lift electromagnet 300 proximate the edges of the poles 304, 308 where the B field has less contribution to the lift. In some configurations, the shaft wall 510 may be tapered 511 proximate the ends of the lift electromagnet 300. Additionally or alternatively, the shaft wall 510 may be narrower and/or tapered 511 near the center of the pole 306.

Figure 8:
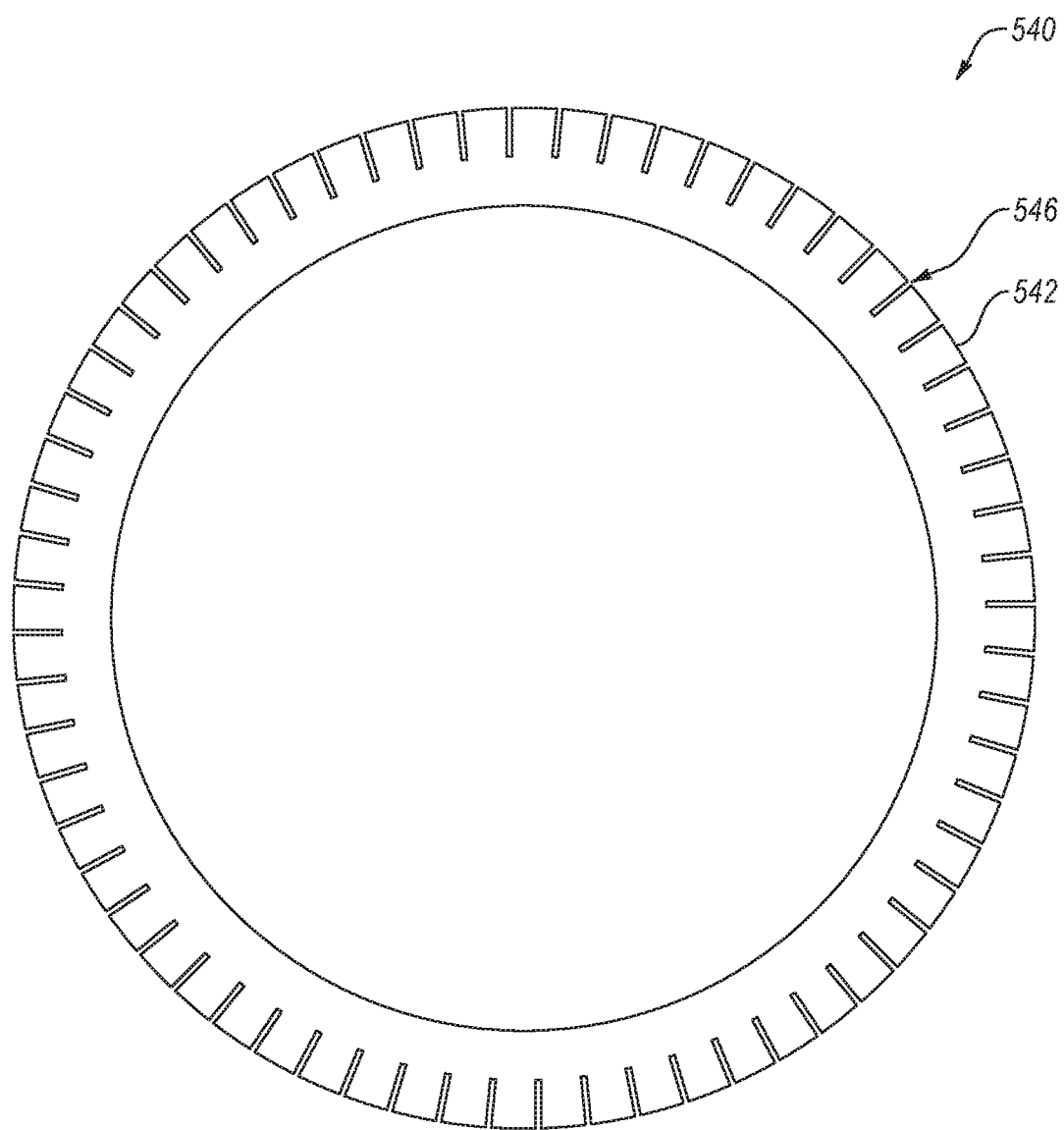
FIG. 8 illustrates a schematic section view of an example embodiment of a lift shaft that may be implemented in lift electromagnets.

In other configurations, rotating mass may be reduced in the shaft wall 502, for example, by adding openings to the shaft wall 502. For example, holes may be drilled into the shaft wall 502 to reduce its rotating mass. In some aspects, the holes or openings may be positioned in the area A5 that has the relatively low B field. In further configurations, slots may be defined in the shaft wall 502. FIG. 8 illustrates an example of a configuration of a lift shaft with slots.

FIG. 8 illustrates a schematic section view of an example embodiment of a lift shaft 540. As shown, in some embodiments the lift shaft 540 may include slots 546 defined in a shaft wall 542. The slots 546 may be parallel to the direction of the B field, and may reduce eddy currents, which are circular electric currents induced within conductors (e.g., metals) by a changing magnetic field in the conductor.

Figure 9:
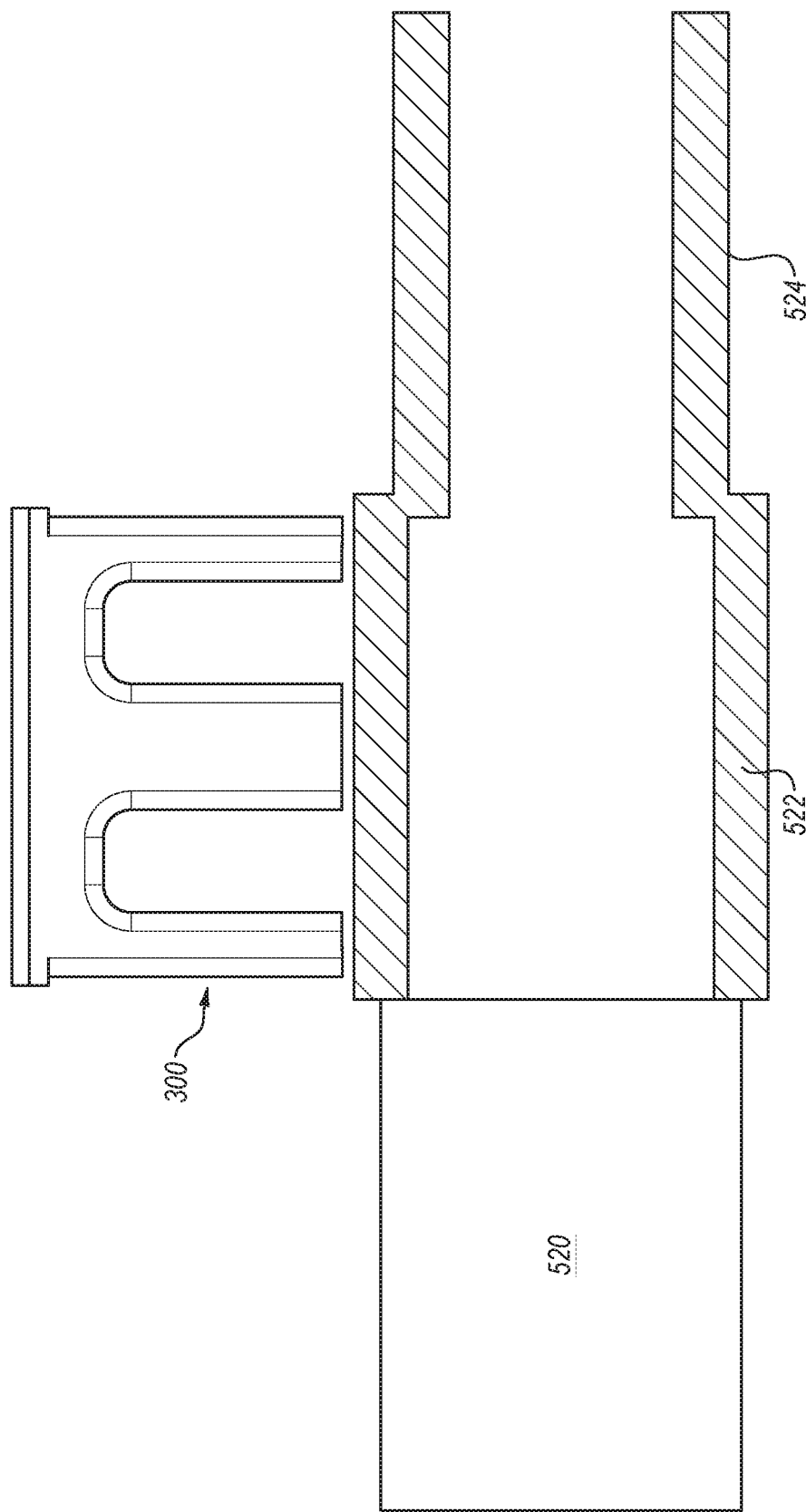
FIG. 9 illustrates a side schematic section view of an example embodiment of a lift shaft integrated with a rotor.

FIG. 9 illustrates a side schematic section view of a lift shaft 522 integrated with a rotor 524. In some configurations, the rotor 524 may be part of an induction motor or motor assembly configured to rotate a rotary anode (see, for example, FIGS. 3A-3B). The rotor 524 may be coupled to a bearing assembly 520 which may permit the lift shaft 522 and the rotor 524 to rotate along with an anode (not shown). The lift shaft 522 is positioned proximate the lift electromagnet 300 to apply a lifting force on the rotating components, which include the rotor 524, the lift shaft 522 and the bearing assembly 520.

As shown, in some configurations, the rotor 524 and the lift shaft 522 may be combined in a monolithic design. In such configurations, the rotor 524 and the lift shaft 522 may not need to be coupled to one another and therefore may not require a coupling or fastening mechanism between the rotor 524 and the lift shaft 522. For example, in some configurations the rotor 524 and the lift shaft 522 may be brazed, welded or bolted to one another. In contrast, when the lift shaft 522 is integrated with the rotor 524, brazing, welding or bolts may not be required. Additionally or alternatively, in such configurations the rotating mass of the rotating components may be reduced, because there is no fastening or coupling structure between the rotor 524 and the lift shaft 522. Further, the overall length of the rotating components may be reduced because there is no fastening or coupling structure between the rotor 524 and the lift shaft 522. Further, the length of the lift shaft 522 can be increased for higher lift force while preserving the overall length of the rotating components.

In some configurations, both the rotor 524 and the lift shaft 522 may be formed or manufactured at the same time, for example, out of a single piece of material. In the illustrated configuration, the rotor 524 includes an inner diameter and an outer diameter that is smaller than a corresponding inner and outer diameter of the lift shaft 522. However, in other configurations the diameters of the lift shaft 522 may be substantially the same or similar sizes to the corresponding diameters of the rotor 524.

Figure 10:
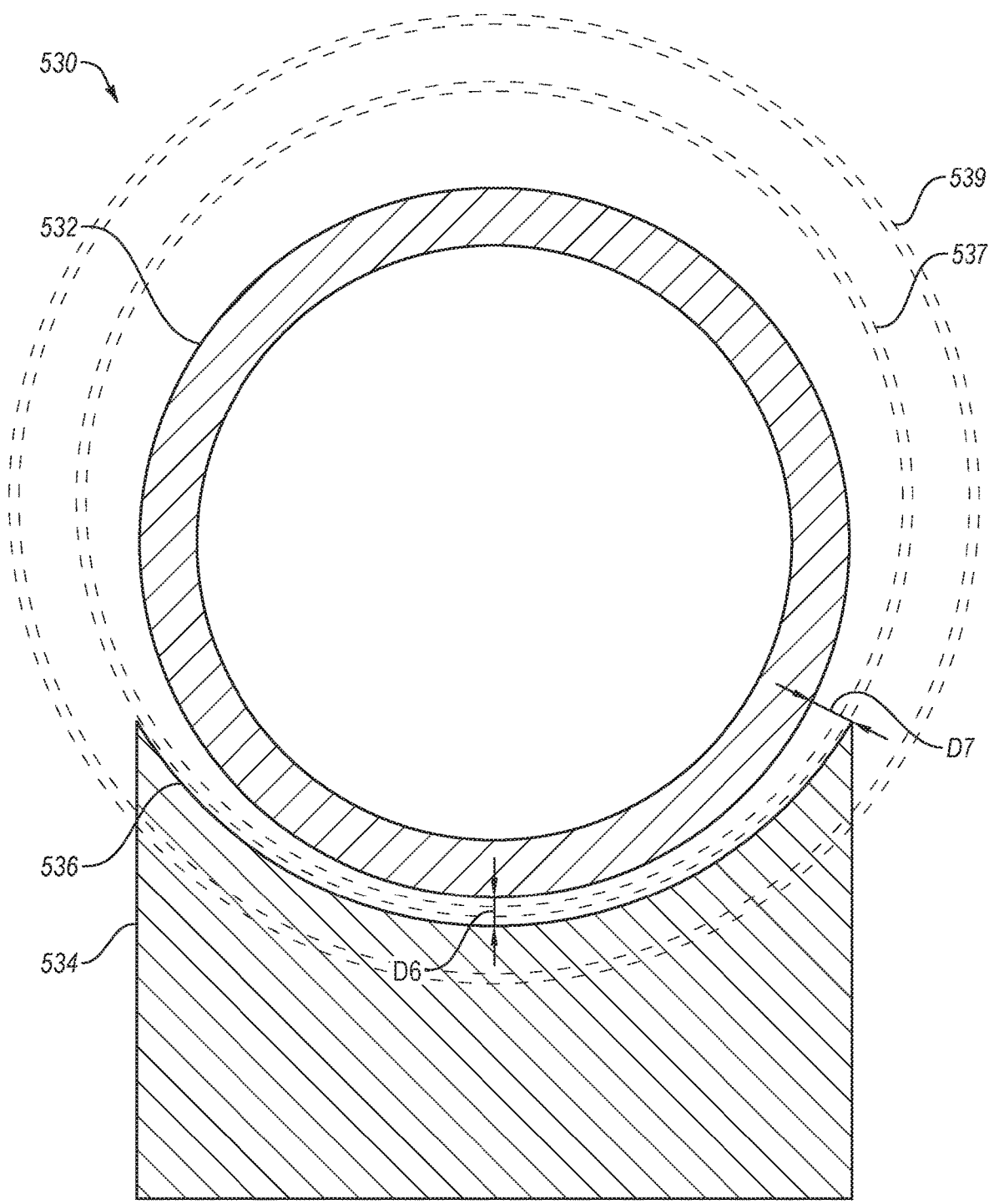
FIG. 10 illustrates a schematic section view of an example embodiment of a lift shaft and a lift electromagnet.

FIG. 10 illustrates a schematic section view of an example embodiment of a lift shaft 530 and a lift electromagnet 534. The lift shaft 530 is substantially cylindrical, with a circular shaft wall 532 with an annular cross-section. As illustrated, the lift electromagnet 534 may include a cylindrical or curved surface 536 that contours with the circular shape of the shaft wall 532. However, the spacing between the curved surface 536 of the lift electromagnet 534 and the shaft wall 532 may be non-uniform. Further, a radius of curvature of the curved surface 536 of the lift electromagnet 534 may be greater than a radius of curvature of the shaft wall 532 of the lift shaft 530. In such configurations, a distance D6 between the curved surface 536 and the shaft wall 532 at central position may be smaller than a distance D7 between the curved surface 536 and the shaft wall 532 proximate the sides of the lift electromagnet 534. Further, the distance between the curved surface 536 and the shaft wall 532 may increase away from the center of the lift electromagnet 534.

In some configurations, the distance D7 may be between 1%-30% or between 10%-20% larger than the distance D6. In further configurations, the distance D7 may be between 0.02 and 5 mm larger than the distance D6. In one example, the distance D6 may be 1.0 mm and the distance D7 may be 1.1 mm. In another example, D7 may be 100 microns or more larger than D6. Additionally or alternatively, the curvature of the curved surface 536 may not be concentric with the curvature of the shaft wall 532.

In configurations where the distance D6 is smaller than the distance D7, the force exerted by the lift electromagnet 534 on the lift shaft 530 is greater in the center than it is on the sides, because the sides are positioned further away from the lift shaft 530. Such configurations may facilitate in retaining and/or positioning the lift shaft 530 in a central position with respect to the lift electromagnet 534. Additionally or alternatively, such configurations may facilitate in avoiding the lift electromagnet 534 and the lift shaft 530 contacting one another, which could prevent the lift shaft 530 from rotating freely and may create rotational drag, and may generate particles in the vacuum which may lead to high voltage instability.

In contrast, if the distance D7 was less than the distance D6, the force at the sides of the lift electromagnet 534 would be greater than the force at the center. In such configurations, if the lift shaft 530 was positioned off-center with respect to the lift electromagnet 534, then the force of the lift electromagnet 534 may pull the lift shaft 530 to the side, which may result in the lift shaft 530 contacting the lift electromagnet 534 or an insert wall 537, if the insert wall 537 is positioned between the lift shaft 530 and the lift electromagnet 534. Accordingly, the configuration shown in FIG. 10 may permit the lift shaft 530 to rotate freely and may minimize rotational drag. In some configurations, the variation between the distance D6 and the distance D7 may be determined based on assembly tolerances and manufacturing tolerances of the lift shaft 530 and the lift electromagnet 534, for example, to ensure that the two components do not touch one another.

In some configurations, a vacuum wall or the insert wall 537 may be positioned between the lift shaft 530 and the lift electromagnet 534. In such configurations, the lift electromagnet 534 may be positioned outside of the vacuum enclosure and the lift shaft 530 and may be positioned inside the vacuum enclosure. The lift electromagnet 534 may apply a lift force on the lift shaft 530 through the insert wall 537. In other configurations, the lift electromagnet 534 and/or the poles of the lift electromagnet 534 may extend through the vacuum wall or an insert wall, as shown by the vacuum wall or an insert wall 539, which includes the lift electromagnet 534 extending there through. In such configurations, the lift electromagnet 534 may extend between and an exterior of the vacuum enclosure and an interior of the vacuum enclosure. As shown, in some configurations the lift wall 537 and/or the lift wall 539 may be non-concentric with the lift shaft 530. In other the lift wall 537 and/or the lift wall 539 may be concentric with the lift shaft 530.

In some configurations, a lift assembly or an X-ray source may include a sensor that measures force, acceleration, magnetic field, or load. For example, the sensor may include a load cell, an accelerometer, a gaussmeter, a hall sensor, a magnetometer, a magnetic sensor, or other suitable sensor. The sensor may be positioned inside or outside the source housing. The sensor may be used to determine the forces exerted on the rotating components or the X-ray source from the rotating of the gantry. The sensor may detect and/or be used to control the force applied by the lift assembly based on a known relationship between force and magnetic field.

Additionally or alternatively, the lift assembly may include a magnetic sensor that measures the magnetic field generated by the lift electromagnet. For example, the magnetic sensor may include a hall effect sensor or other suitable magnetic sensor. The magnetic sensor may be positioned between the lift electromagnet and the housing of the X-ray source. The force of the lift electromagnet may be controlled in response to information received from the force sensor, the magnetic sensor, or both. In one example, the force of the lift electromagnet may be controlled by using the magnetic sensor to monitor the B field produced by the lift electromagnet, and varying the output of the lift electromagnet proportionally to the B field or the b field squared.

Additionally or alternatively, the force of the lift electromagnet may be controlled by using the force sensor to monitor the force on the rotating components or the X-ray source caused by the rotation of the gantry. In such configurations, the output of the lift electromagnet may be adjusted based on the forces exerted from the rotation of the gantry. For example, the lift force generated by the lift electromagnet may be balanced or matched with the force caused by the rotation of the gantry, thereby effectively cancelling this force, or at least reducing the force.

Figure 11:
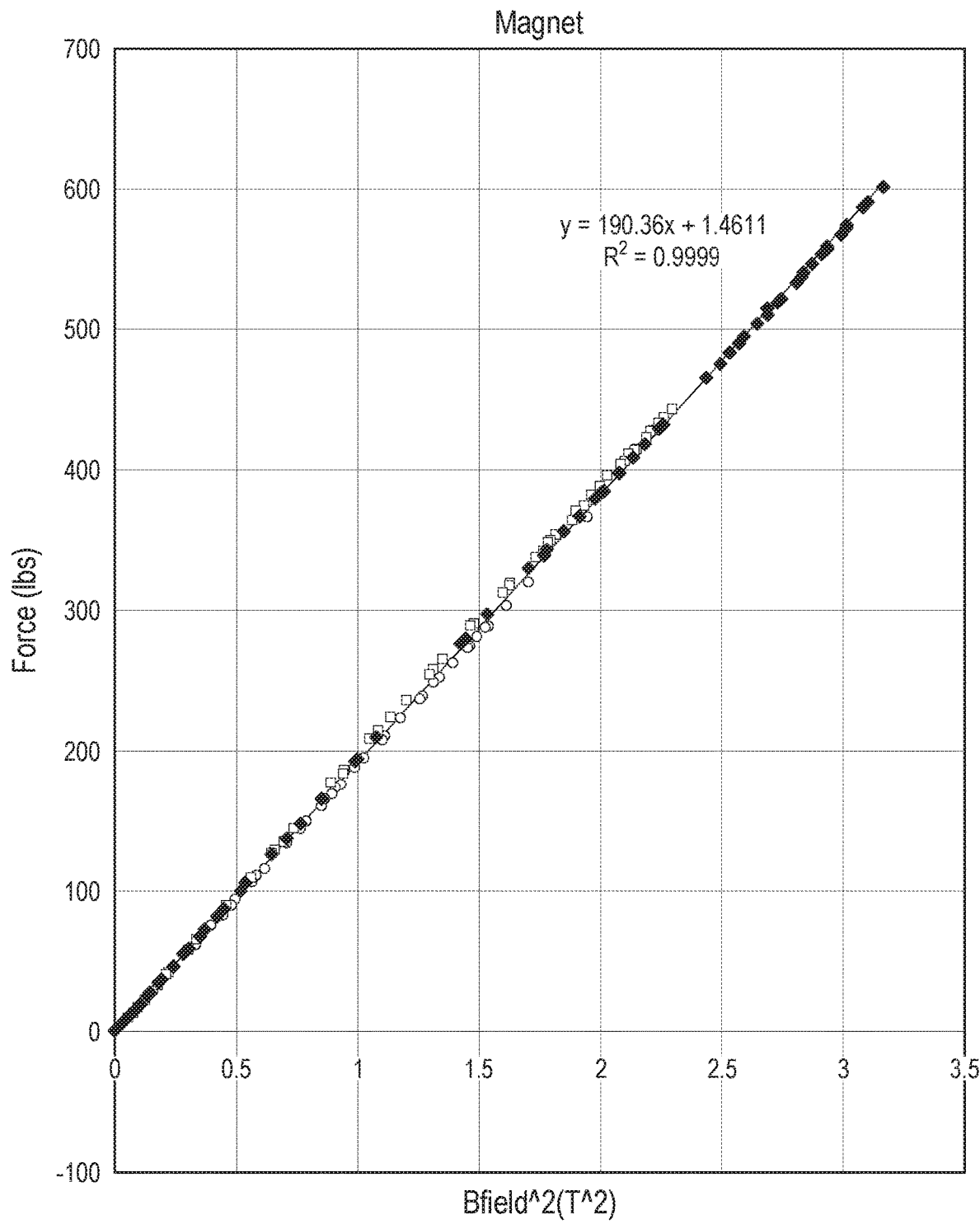
FIG. 11 is a graph depicting an example of the relationship of the force of a lift electromagnet, in units of pounds (lbs), versus the square of the B field ($T^2$).

FIG. 11 illustrates a graph depicting the relationship of the force of the lift electromagnet, in units of pounds (lbs), versus the square of the B field ($T^2$). As illustrated, the square of the B field has a linear relationship with respect to the force of the lift electromagnet. This relationship may be used to control the lift electromagnet based on information from the force sensor and/or the magnetic sensor.

Figure 12A:
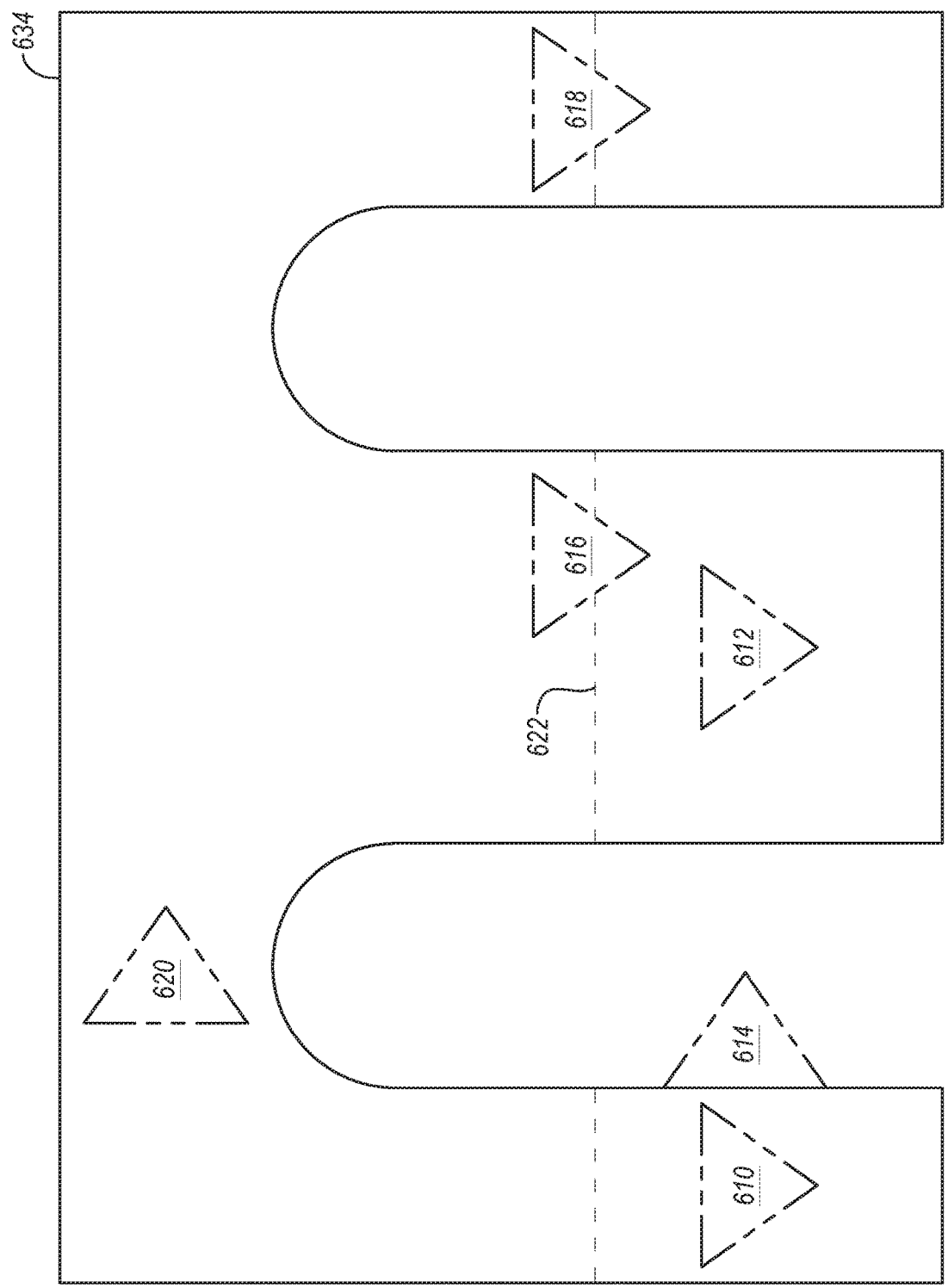
FIG. 12A illustrates a schematic section view of an example embodiment of a lift shaft and a lift electromagnet including sensors.
Figure 12B:
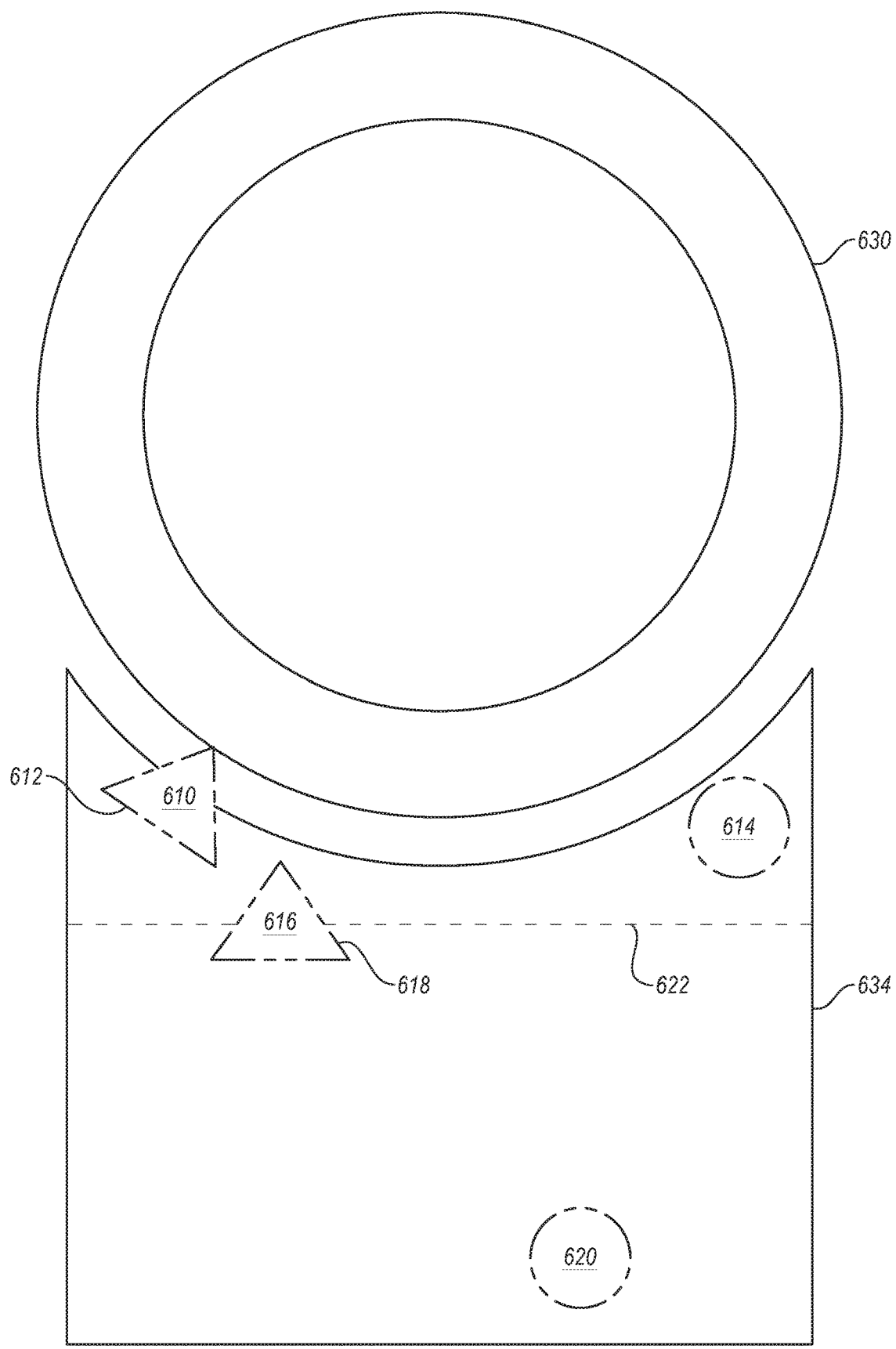
FIG. 12B illustrates a side view of an example embodiment of a lift electromagnet including sensors.

FIGS. 12A-12B illustrate an example embodiment of a lift electromagnet 634 that includes one or more sensors that may be used to control lift force. In particular, FIG. 12A illustrates a side view of an example embodiment of the lift electromagnet 634 and FIG. 12B illustrates a schematic section view of the lift electromagnet 634.

As shown in FIGS. 12A-12B, the lift electromagnet 634 may include one or more sensors, such as sensors 610, 612, 614, 616, 618 and 620 that may be positioned in various areas of the lift electromagnet 634. Sensors are represented as cones FIGS. 12A-12B, so a triangle represents a side view of the sensor and a circle represents a top or bottom view of the sensor. For example, FIG. 12A illustrates a side view of sensors 614 and 620, and FIG. 12B illustrates a top view of sensors 614 and 620. As shown, the sensor 620 is embedded in or positioned on the core of the lift electromagnet 634. The sensors 610, 612, 614, 616, 618 are positioned on or proximate to the poles of the lift electromagnet 634. The sensors 610 and 614 are positioned on one of the poles on the end of the lift electromagnet 634, while the sensor 612 is positioned on the pole in the center of the lift electromagnet 634. The sensors 616, 618 are positioned at or proximate an interface 622 between an interior of a vacuum envelope and an exterior of the vacuum envelope. Additionally or alternatively, sensors may be positioned proximate the insert wall or at a position where the insert wall is coupled to the lift electromagnet 634. Some of the sensors, such as the sensors 610, 612, and 614, may be positioned inside of a vacuum envelope or in an evacuated enclosure. Other sensors, such as the sensors 616, 618, and 620, may be positioned outside of the vacuum envelope or the evacuated enclosure. In some configurations, the sensors 610, 612, 614, 616, 618 positioned on the poles may be embedded in the windings (not shown) of the lift electromagnet 634. In other configurations, the sensors 610, 612, 614, 616, 618 may be positioned over the windings. In some configurations, the sensors may measure a "fringe" field that travels directly between two poles without going through a lift shaft 630.

Figure 13:
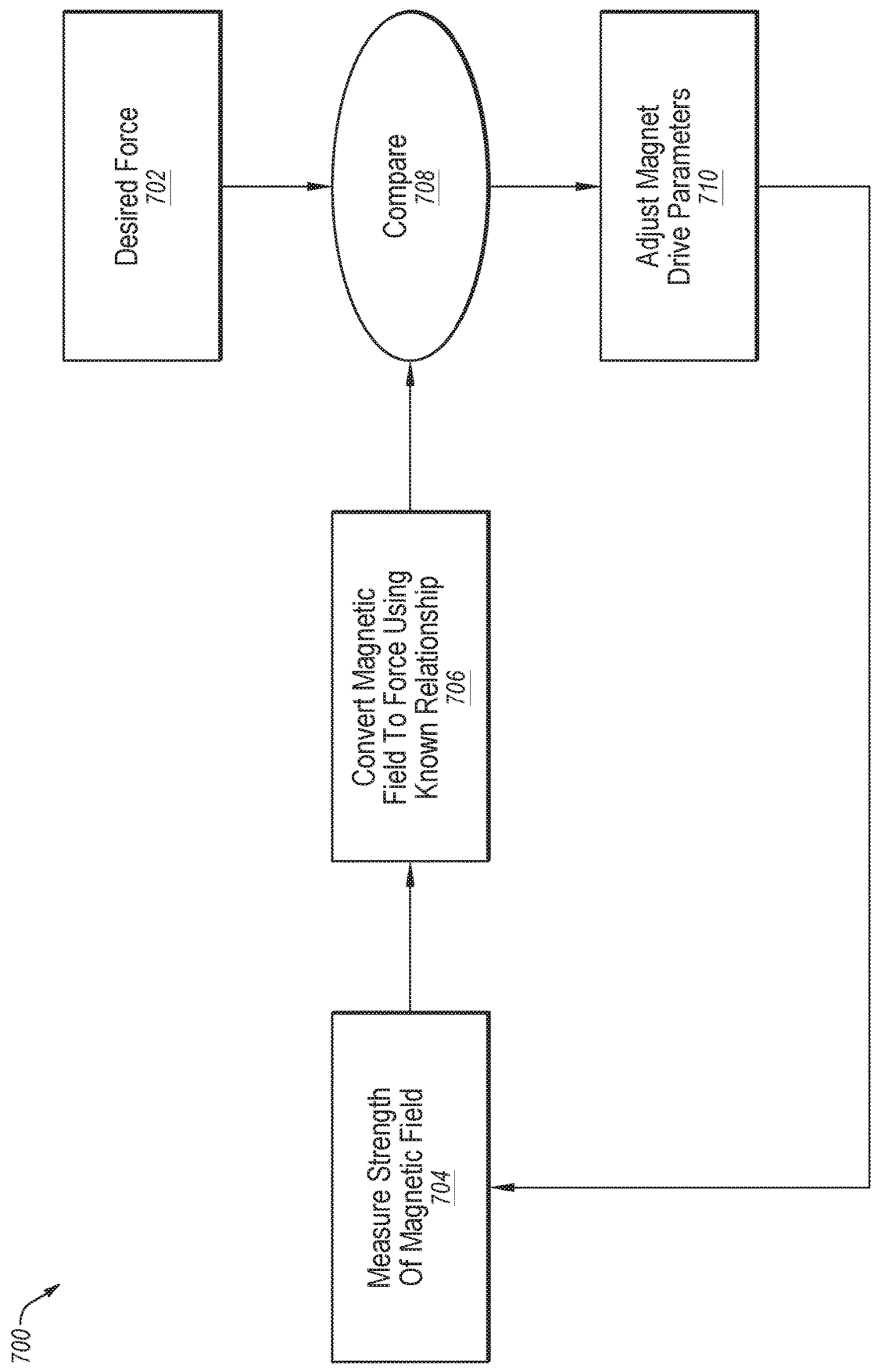
FIG. 13 is a flow chart of an example method for manufacturing a lift electromagnet.

FIG. 13 is a flow chart of an example method 700 for controlling a lift electromagnet. At step 702, a desired force may be obtained. As will be described in further detail below, the desired force may be obtained based on information, data, or a force obtained or detected by one or more sensors, such as the sensors 610, 612, 614, 616, 618, 620 described above with respect to FIGS. 12A-12B. In some circumstances, the sensor may be used to determine the forces exerted on the rotating components or the X-ray source from the rotating of the gantry. The sensor may detect and/or be used to control the force applied by the lift assembly based on a known relationship between force and magnetic field. For example, the force applied by the lift assembly may be controlled based on the relationship between force and magnetic field shown and described above with respect to FIG. 11, and based on the force detected by the sensor.

At step 704, the strength of a magnetic field may be measured. For example, the strength of a magnetic field may be measured by one or more sensors, such as the sensors 610, 612, 614, 616, 618, 620 described above with respect to FIGS. 12A-12B. At step 706, the measured magnetic field may be converted to force using a known relationship, such as the relationship between force and magnetic field shown and described above with respect to FIG. 11. After step 706, the method 700 may proceed to step 708, where the desired force may be compared to the converted force determined based on the known relationship. At step 710, the magnet drive parameters may be adjusted. In some embodiments the magnet drive parameters may be adjusted to correspond to or counteract the forces on the on the rotating components or the X-ray source from the rotating of the gantry, as detected by the sensor. The method 700 may continue as necessary to control and/or adjust the force and/or magnetic field output by the lift electromagnet.

For the processes and/or methods disclosed, the functions performed in the processes and methods may be implemented in differing order as may be indicated by context. Furthermore, the outlined steps and operations are only provided as examples, and some of the steps and operations may be optional, combined into fewer steps and operations, or expanded into additional steps and operations.

In one example embodiment, a lift assembly (220) may exert a force on a rotatable anode (122) of an X-ray source (100). The lift assembly (220) may include a lift shaft (226) and a lift electromagnet (222). The lift shaft (226) may be coupled to the anode (122) and configured to rotate around an axis of rotation of the anode (122). The lift electromagnet (222) may be configured to apply a magnetic force to the lift shaft (226) in a radial direction. The lift electromagnet (222) may include a curved surface that contours around at least a portion of the shaft wall (502). A radius of curvature of the curved surface of the lift electromagnet (222) may be greater than a radius of curvature of the lift shaft (226), and the spacing between the curved surface of the lift electromagnet (222) and the shaft wall (502) may be non-uniform.

A first distance between the curved surface and the shaft wall (502) at a center of the lift electromagnet (222) may be smaller than a second distance between the curved surface and the shaft wall (502) proximate an edge of the lift electromagnet (222). The second distance may be between 1%-30% larger than the first distance. The shaft wall (502) may have a non-uniform thickness and/or may include a taper (511) proximate the center or the ends of the lift electromagnet (222). The lift shaft (226) may be integrated with a rotor (524) configured to rotate the anode (122).

The lift electromagnet (222) may include at least one pole (304, 306, 308) that includes rounded portions and windings 310, 312, 314 positioned around the rounded portions of the pole (304, 306, 308).

The lift electromagnet (222) may include a first pole (304) having a first cross sectional area, a second pole (306) having a second cross sectional area, and a third pole (308) having a third cross sectional area. The second cross sectional area may be at least 1½ times the first cross sectional area or the third cross sectional area. The second cross sectional area may be 1%-100% larger than two times the first cross sectional area or the third cross sectional area. The second cross sectional area may be substantially the same size as or larger than the first cross sectional area and the third cross sectional area added together, and the first cross sectional area and the third cross sectional area may be substantially the same.

Windings 310, 312, 314 may be positioned around at least one of the first pole (304), the second pole (306), or the third pole (308), wherein the windings 310, 312, 314 include a circular, elliptical, rectangular, or high aspect ratio rectangular cross-section. A rounded portion may couple the first pole (304), the second pole (306), or the third pole (308) to a core of the lift electromagnet (222). The first pole (304), the second pole (306), or the third pole (308) may be configured to operate at or near saturation.

The lift assembly (220) may include at least one sensor that measures force, acceleration, magnetic field, or load. The sensor may be embedded in a core of the lift electromagnet (222), embedded in windings 310, 312, 314 of the lift electromagnet (222), positioned on a pole of the lift electromagnet (222), or positioned proximate an interface between an interior of a vacuum envelope and an exterior of the vacuum envelope.

A shaft wall (502) of the lift shaft (226) may include a thickness sufficient for the lift shaft (226) to operate at or near saturation.

In another embodiment a method may include rotating an anode assembly (120) of an X-ray source (100), determining a force, acceleration or load acting on the rotating anode assembly (120), and applying a magnetic force by a lift electromagnet (222) to a lift shaft (226) coupled to the anode assembly (120) based on the force, acceleration or load acting on the rotating anode assembly (120). More of the magnetic force may be applied at a center of the lift electromagnet (222) than on an edge of the lift electromagnet (222). The method may include operating the lift electromagnet (222) at or near saturation. The force, acceleration or load may be determined by a sensor coupled to the lift electromagnet (222).

In another embodiment, a lift assembly (220) may be configured to exert a force on a rotatable anode (122) of an X-ray source (100). The lift assembly (220) may include a lift shaft (226) coupled to the anode (122) and configured to rotate around an axis of rotation of the anode (122). The lift shaft (226) may include a shaft wall (502). The lift assembly (220) may include a lift electromagnet (222) comprising means for applying a magnetic force to the lift shaft (226) in a radial direction, wherein more of the magnetic force is applied at a center of the lift electromagnet (222) than on an edge of the lift electromagnet (222).

The terms and words used in this description and claims are not limited to the bibliographical meanings, but, are merely used to enable a clear and consistent understanding of the disclosure. It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those skilled in the art, may occur in amounts that do not preclude the effect the characteristic was intended to provide.

Aspects of the present disclosure may be embodied in other forms without departing from its spirit or essential characteristics. The described aspects are to be considered in all respects illustrative and not restrictive. The claimed subject matter is indicated by the appended claims rather than by the foregoing description. All changes which come within the meaning and range of equivalency of the claims are to be embraced within their scope.

What is claimed is:

1. A lift assembly configured to exert a force on a rotatable anode of an X-ray source, the lift assembly comprising:

a lift shaft coupled to the anode and configured to rotate around an axis of rotation of the anode, the lift shaft comprising a shaft wall; and a lift electromagnet configured to apply a magnetic force to the lift shaft in a radial direction, the lift electromagnet comprising a curved surface that contours around at least a portion of the shaft wall;

wherein a radius of curvature of the curved surface of the lift electromagnet is greater than a radius of curvature of the lift shaft, wherein the spacing between the curved surface of the lift electromagnet and the shaft wall is non-uniform.

2. The lift assembly of claim 1, wherein a first distance between the curved surface and the shaft wall at a center of the lift electromagnet is smaller than a second distance between the curved surface and the shaft wall proximate an edge of the lift electromagnet.

3. The lift assembly of claim 1, wherein the second distance is between 1%-30% larger than the first distance.

4. The lift assembly of claim 1, wherein the shaft wall has a non-uniform thickness.

5. The lift assembly of claim 1, wherein the shaft wall comprises a taper proximate the center or the ends of the lift electromagnet.

6. The lift assembly of claim 1, wherein the lift shaft is integrated with a rotor configured to rotate the anode.

7. The lift assembly of claim 1, further comprising at least one sensor that measures force, acceleration, magnetic field, or load.

8. The lift assembly of claim 7, where the sensor is:
embedded in a core of the lift electromagnet;
embedded in windings of the lift electromagnet;
positioned on a pole of the lift electromagnet; or
positioned proximate an interface between an interior of a vacuum envelope and an exterior of the vacuum envelope.

9. The lift assembly of claim 1, the lift electromagnet further comprising:
a first pole having a first cross sectional area;
a second pole having a second cross sectional area; and
a third pole having a third cross sectional area;
wherein the second cross sectional area is at least 1½ times the first cross sectional area or the third cross sectional area.

10. The lift assembly of claim 9, wherein the second cross sectional area is 1%-100% larger than two times the first cross sectional area or the third cross sectional area.

11. The lift assembly of claim 9, wherein the second cross sectional area is substantially the same size as or larger than the first cross sectional area and the third cross sectional area added together, and the first cross sectional area and the third cross sectional area are substantially the same.

12. The lift assembly of claim 9, further comprising windings positioned around at least one of the first pole, the second pole, or the third pole, wherein the windings include a circular, elliptical, rectangular, or high aspect ratio rectangular cross-section.

13. The lift assembly of claim 9, further comprising a rounded portion coupling the first pole, the second pole, or the third pole to a core of the lift electromagnet.

14. The lift assembly of claim 1, wherein the lift electromagnet comprises:
at least one pole that includes rounded portions; and
windings positioned around the rounded portions of the pole.

15. The lift assembly of claim 1, wherein a shaft wall of the lift shaft includes a thickness sufficient for the lift shaft to operate at or near saturation.

16. A method comprising:
- rotating an anode assembly of an X-ray source;
- determining a force, acceleration or load acting on the rotating anode assembly; and
- applying a magnetic force by a lift electromagnet to a lift shaft coupled to the anode assembly based on the force, acceleration or load acting on the rotating anode assembly, wherein more of the magnetic force is applied at a center of the lift electromagnet than on an edge of the lift electromagnet.

17. The method of claim 16, wherein the force, acceleration or load is determined by a sensor coupled to the lift electromagnet.

18. The method of claim 16, further comprising operating the lift electromagnet at or near saturation.

19. A lift assembly configured to exert a force on a rotatable anode of an X-ray source, the lift assembly comprising:
- a lift shaft means coupled to the anode for rotating around an axis of rotation of the anode, the lift shaft comprising a shaft wall; and
- a lift electromagnet means for applying a magnetic force to the lift shaft in a radial direction, wherein more of the magnetic force is applied at a center of the lift electromagnet than on an edge of the lift electromagnet.

20. The lift assembly of claim 19, wherein a radius of curvature of a curved surface of the lift electromagnet means is greater than a radius of curvature of the lift shaft means.

* * * * *